United States Patent [19]

Vishwakarma

[11] Patent Number: 5,455,152
[45] Date of Patent: Oct. 3, 1995

[54] BENZOTRIAZOLE BASED UV ABSORBING MONOMERS AND PHOTOGRAPHIC ELEMENTS CONTAINING POLYMERS FORMED FROM THEM

[75] Inventor: Lal C. Vishwakarma, Rochester, N.Y.

[73] Assignee: Eastman Kodak Company, Rochester, N.Y.

[21] Appl. No.: 313,492

[22] Filed: Sep. 27, 1994

[51] Int. Cl.$^6$ ................................................. G03C 1/815
[52] U.S. Cl. ........................ 430/512; 430/627; 430/630; 430/631; 430/496
[58] Field of Search .................................. 430/512, 627, 430/630, 631, 496

[56] References Cited

U.S. PATENT DOCUMENTS

| | | | |
|---|---|---|---|
| 3,072,585 | 1/1963 | Milionis et al. | 430/512 |
| 3,213,058 | 10/1965 | Boyle et al. | 528/96 |
| 3,214,436 | 10/1965 | Boyle et al. | 548/260 |
| 3,698,907 | 10/1972 | Sato et al. | 430/512 |
| 4,785,063 | 11/1988 | Slongo et al. | 526/259 |
| 4,885,396 | 12/1989 | Hahn et al. | 568/315 |
| 5,032,498 | 7/1991 | Rody et al. | 430/512 |
| 5,234,807 | 8/1993 | Texter et al. | 430/627 |
| 5,372,922 | 12/1994 | Schofield et al. | 430/572 |

FOREIGN PATENT DOCUMENTS

| | | |
|---|---|---|
| 135118 | 11/1970 | Czechoslovakia . |
| 0190003 | 8/1986 | European Pat. Off. . |
| 0577122 | 1/1994 | European Pat. Off. ............... 430/512 |
| 04198148-A | 11/1990 | Japan . |

OTHER PUBLICATIONS

Synthesis, Manfred Lissel, Stefan Schmidt, Beate Neumann, "Dimethylcarbonat als Methylierungsmittel unter phasen–transfer–katalytischen Bedingungen," May 1986, pp. 382–383, Communications.

*Primary Examiner*—Thomas R. Neville
*Attorney, Agent, or Firm*—Gordon M. Stewart

[57] ABSTRACT

An ultraviolet absorbing monomer of formula (A):

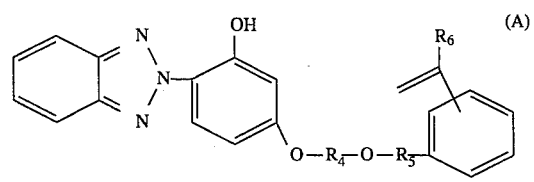

wherein: $R_4$ and $R_5$ are, independently, a substituted or unsubstituted alkylene with or without intervening oxygen, sulfur or nitrogen atoms; $R_6$ is H or a substituted or unsubstituted methyl; and the benzo ring, the hydroxy substituted phenyl ring and the phenyl ring of the styryl group may be further substituted or unsubstituted. A method of making such monomers and photographic elements containing UV absorbing polymers formed from such monomers are also provided.

12 Claims, 5 Drawing Sheets

—— CONVENTIONAL (IIA+IIB) UV ABSORBING MIXTURE
········ MONOMER OF FORMULA (A)

BENZOTRIAZOLE BASED UV ABSORBING MONOMERS AND PHOTOGRAPHIC ELEMENTS CONTAINING POLYMERS FORMED FROM THEM

FIELD OF THE INVENTION

This invention relates to particular benzotriazole based UV absorbing monomers, a photographic element containing UV absorbing polymers formed from them, and a method of making the monomers.

BACKGROUND

Typical photographic elements use silver halide emulsions, the silver halide having a native sensitivity to ultraviolet radiation. Ultraviolet radiation ("UV") as used in this application means light having a wavelength of 300–400 nm. Such UV sensitivity is usually undesirable in that it produces an image on the photographic element which is not visible to the human eye. Furthermore, the image dyes in the color photographs are known to fade due to action of UV light. Also other organic molecules such as unused color forming couplers in the emulsion layers and optical brightners in the paper support degrade due to action of UV light and generate undesirable color stains on the finished photographs. Therefore, photographic elements typically contain a UV absorbing compound (sometimes referred to simply as a "UV absorber"). Another function of UV absorbers is to prevent the formation of undesirable patterns caused by electrostatic discharge in silver halide photographic materials. In general, UV absorbers impart light stability to organic molecules in various products which are susceptible to degrade as a result of the action of UV.

Generally, an effective UV absorber should have its peak absorption above a wavelength of 320 nm. The absorption peak may be at a longer wavelength, as long as absorption drops off sufficiently as it approaches the visual range (approximately 400 to 700 nm) so that no visible color is shown by the compound. In addition, to be effective, a UV absorber should have a high extinction coefficient in the desired wavelength range. However, for the most desirable UV protection, the high extinction coefficient should be at those wavelengths sufficiently below the visual range so that the compound should not be visually yellow.

Both conventional and polymeric UV absorbers have been used in photographic elements. Examples of conventional (that is, non-polymeric) UV absorbing compounds are shown by formula (II A) and (II B) below, currently used in color paper as a mixture have the following structures.

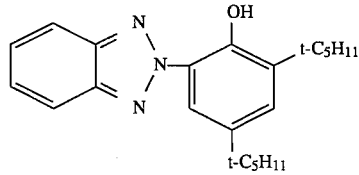

(II A)

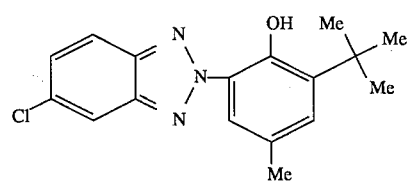

(II B)

It has however, been observed that these compounds and other non-polymeric UV absorbers have a propensity to crystallize out in the coatings. This results in migration of the compound to the surface causing an undesirable blooming effect. Recently, it has been suggested that such compounds are associated with high health risk factors.

The benzotriazole class of polymers having monomeric units from formula (III) below, their synthesis, and use in various plastic formulations, are described in U.S. Pat. No. 3,072,585.

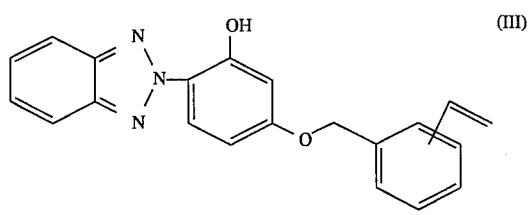

(III)

EP-A-0 190 003 B1 describes photographic elements containing polymers of formula (III). Photographic elements containing other polymers of formula (IV) below are disclosed in allowed U.S. patent application 07/907,008 by Chen et al. filed Jul. 1, 1992.

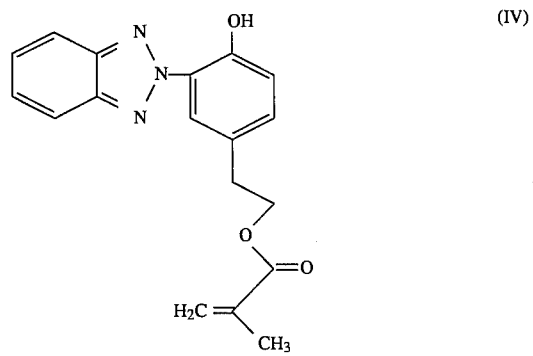

(IV)

Polymers of formula (III) and (IV) are highly useful in photographic elements. However, they tend to have a hypsochromically shifted (that is, shifted to shorter wavelengths) absorbance position in silver halide photographic elements, with respect to current photographic element dispersions of conventional UV absorbers of formula (IIA) and (IIB). Although this hypsochromic shift allows optical brightners on a paper support to act more efficiently for an increased whiteness, it allows sufficient UV light to reach image dyes and optical brightening molecules causing their photolytic degradation. Many magenta image dyes are also more prone to such degradation with a hypsochromically shifted UV absorber.

An additional problem with the monomer (III) has been the cost associated with its synthesis. The monomer (III) is generated by alkylating its precursor (V) with moderately expensive vinyl benzyl chloride. In addition to its expense, the yield of the monomer (III) is lowered due to formation of the dialkylated by-product (VI) even under carefully controlled monoalkytation procedures reported in the literature.

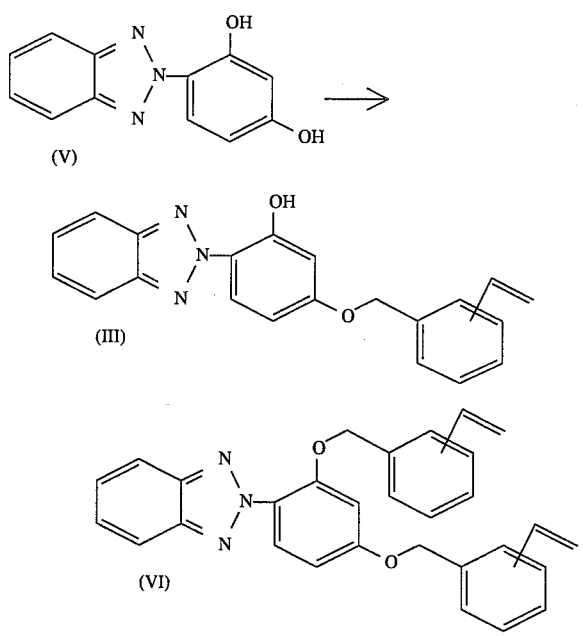

U.S. Pat. No. 3,213,058 though, does mention the conversion of (V) to (VII) using base-catalyzed alkylation with chloroethanol or bromoethanol or ethylene oxide under higher temperature/pressure condition.

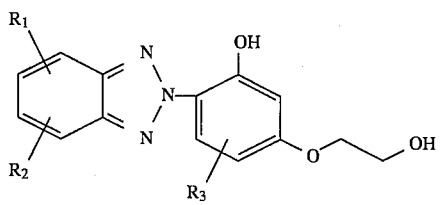

The use of ethylene carbonate (VIII):

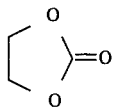

to attach a hydroxyethyl substituent has been known in various chemical reactions. In particular, it was described for use with benzophenones in U.S. Pat. No. 4,885,396; in the hydroxyethylation of thiophenol, Y. Tamura, et al, *Synthesis*, 641 (1975); in the hydroxyethylation of thiophenol using 18-Crown-6 as a catalyst, M. Lissel, S. Schmidt and B. Neumann, Synthesis-Stuttgart (5), 382–383 (1986); and in the hydroxyethylation of perfluroalkanol S. M. Heilman L. R. Krepski, D. M. Moren, and J. K. Rasmussen, U.S. Pat. 4,906,792.

It is desirable then to have additional classes of UV absorbers from which one can select for various applications, particularly for photographic uses. It is additionally desirable, although not necessary, to design new UV monomeric absorbers which would have an absorbance position close to or slightly better than the currently used combination of UV compounds (II A) and (II B) while maintaining the effect from optical brightening compounds. It is additionally desirable that the compound can be readily made in good yields with low levels of unwanted products.

SUMMARY OF THE INVENTION

The present invention therefore provides an ultraviolet absorbing compound of formula (A):

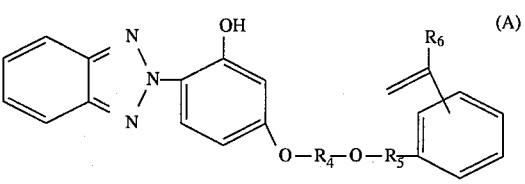

wherein: $R_4$ and $R_5$ are, independently, a substituted or unsubstituted alkylene with or without intervening oxygen, sulfur or nitrogen atoms; $R_6$ is H or a substituted or unsubstituted methyl; and the benzo ring, the hydroxy substituted phenyl ring, and the phenyl ring of the styryl group may be further substituted or unsubstituted. However, any substituents should not have unsaturated carbon-carbon bonds.

The present invention further provides a photographic element containing polymers having repeating units formed from the monomer of formula (A).

The present inventor recognized that in addition to designing a new class of polymeric UV absorbers to meet one or more of the above needs, it was also necessary to develop an appropriately functionalized precursor monomeric compound which would allow a polymerizable group to be attached with high preference to one position of the monomeric compound. To accomplish this a precursor of compound (A) can be used in which the vinyl benzyl group is not present and $R_5$ is replaced with —OH to provide a terminal hydroxy group. More specifically, a precursor such as (VII) was selected in which a polymerizable group could be attached with a high degree of preference to the oxygen atom of the primary alcoholic group during the alkylation step. It was recognized that reactivity of the alkoxide anion involving $S_N2$ type nucleophilic displacement will be much greater with respect to the phenoxide anion present in the same molecule.

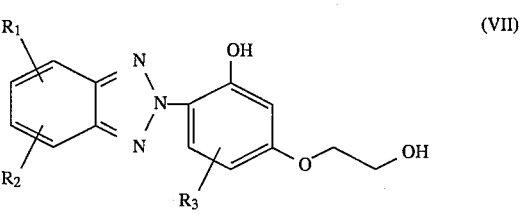

Further, UV monomers derived from (VII) will provide polymers of lower $T_g$ values (that is lower than about 80° C.) by virtue of containing a flexible longer side chain. This feature may contribute to their increased intrinsic light stability.

The present invention then, also generally provides a method for conveniently and economically making monomeric compounds of formula (D) below:

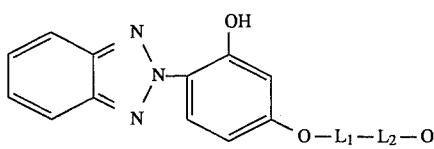

(D)

wherein: the benzo ring and the hydroxy substituted phenyl ring may each be further substituted as described in formula (A) above, and more particularly may be substituted with 1 to 4 substituents which are, independently, 1 to 18 carbon alkyl, aryl, heteroaryl, aryloxy or alkoxy, or halogen, or the benzo may have a benzo, pyrrolo, furyl or thienyl ring fused thereto, and the alkyl and alkoxy substituents may have 1 to 5 intervening oxygen, sulfur or nitrogen atoms; $L_1$ and $L_2$ are, independently, methine or methine substituted with 1–6 carbon alkyl, alkoxy, or halogen. The method comprises reacting the dihydroxy compound corresponding to formula (D) with ethylene carbonate of the formula:

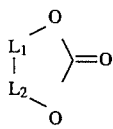

wherein $L_1$ and $L_2$ are the same as previously defined.

The compounds of formula (D) are then used to synthesize new UV absorbing monomers of formula (A) in which $R_4$ is substituted or unsubstituted ethylene, not only for their use in light sensitive silver halide photographic elements but in general for any product needing UV light protection.

DRAWINGS

EMBODIMENTS OF THE INVENTION

Figure 1:
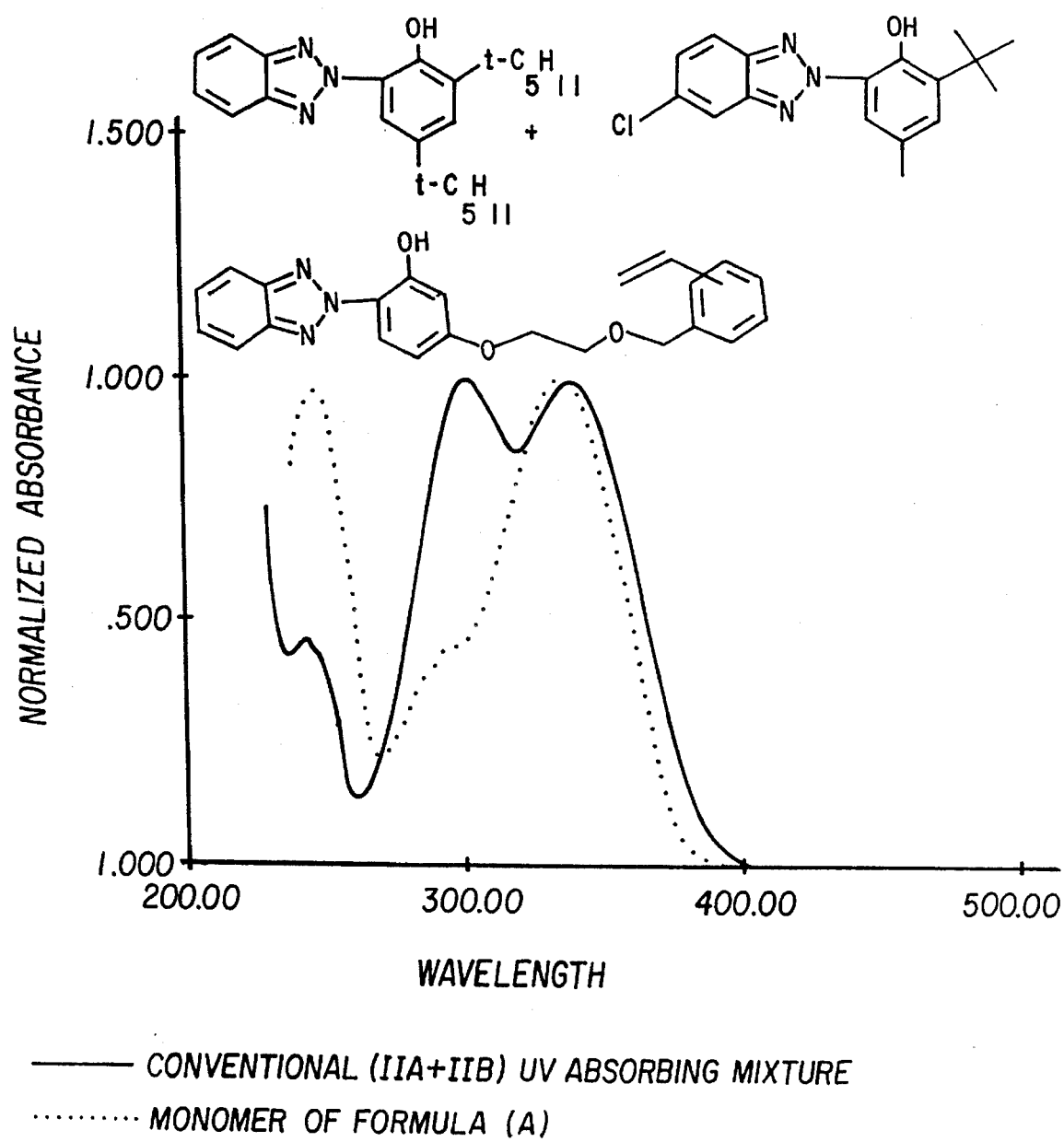
FIG. 1 shows the normalized absorbance spectra, in solution, of the monomer Compound No. XIX-1 of the present invention, described below and a mixture of commonly used UV absorbers IIA and IIB, described below.

Monomers of formula (A) and polymers having monomeric units formed from such monomers can provide superior spectral features for a UV absorber. In particular, they can have a sharper drop off in absorption at longer UV wavelengths and higher extinction coefficients with respect to the conventionally used UV absorbing monomeric compounds (IIA) and (IIB) above. Higher extinction coefficients mean less amount of material needs to be coated in a photographic element for the same UV absorption, thereby improving cost effectiveness of the material. Since a polymer latex formed from a monomer of formula (A) tends to be visually white then a polymer latex of a monomer of formula (A) is particularly useful in elements of the present invention which are photographic color paper elements since the polymers have only low blue Dmin (that is, blue minimum density). Furthermore, according to current United States Environmental Protection Agency environmental guidelines, the styryl-based UV absorbing polymers formed from monomers of formula (A) would tend to be more environmentally acceptable over their acrylate or acrylamide based counterparts. Also, the method of the present invention provides a relatively economical and environmentally safe process for the synthesis of the precursors of formula (D). Compounds of formula (D) are then used to synthesize the desired new UV absorbing monomers (A) in high yields by selective alkylation of the primary alcoholic group with vinyl benzyl chloride. Thus, relatively low costing monomers of formula (A) are prepared with the same or slightly more bathochromically shifted absorbance position (that is, shifted toward a longer wavelength by about 5–10 nm) with respect to previously reported monomer (III), while still maintaining an acceptable whiteness which can be provided by optical brightners.

In the present application reference to ultraviolet or UV in relation to the present invention refers to the wavelength range of 300 to 400 nm unless the contrary is indicated. Additionally, reference to "under", "above", "below", "upper", "lower" or the like terms in relation to layer structure of a photographic element, is meant the relative position in relation to light when the element is exposed in a normal manner. "Above" or "upper" would mean closer to the light source when the element is exposed normally, while "below" or "lower" would mean further from the light source. Since a typical photographic element has the various layers coated on a support, "above" or "upper" would mean further from the support, while "below" or "under" would mean closer to the support. It will also be understood throughout this application that reference to a compound of a particular general formula includes those compounds of other more specific formula which specific formula falls within the general formula definition.

By "corresponding" in relation to the method of making compounds of the type of formula (D) is meant that —$L_1$—$L_2$—OH is replaced with H to provide the phenyl with a second —OH in the para position with respect to the benzotriazole. For example, a compound of formula (XII) below corresponds to a compound of formula (E) in this context:

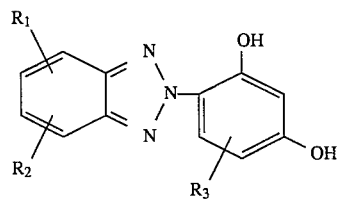

(XII)

In compounds of formula (A), $R_4$ and $R_5$ may particularly each have from 1 to 20 carbon atoms (or 1 to 10, 1 to 6, or 1 to 3 carbon atoms). Each of them may be, independently, an alkylene either of which may be unsubstituted or substituted with a 1 to 10 carbon alkoxy (or 1 to 6, or 1 to 2 carbon alkoxy), a 1 to 10 carbon atom alkyl sulfide (or 1 to 6, or 1 to 2 carbon alkyl sulfide), 0 to 10 carbon amino (or 0 to 6, or 0 to 2 carbon amino), or halogen, and either $R_4$ or $R_5$ may contain 1–5 intervening oxygen, sulfur or nitrogen atoms (or 1 to 2 such intervening atoms); $R_6$ is H, methyl or a methyl substituted with a halogen; and the benzo ring and the hydroxy substituted phenyl ring may each be further substituted with 1 to 4 substituents which are, independently, 1 to 18 carbon alkyl (or 1 to 6, or 1 to 2 carbon alkyl), aryl, heteroaryl (such as pyrrolo, furyl or thienyl), aryloxy or alkoxy, or halogen (for example F or Cl, particularly on the benzo ring at 5 or 6 position for Cl, on the hydroxy substituted phenyl at 5' for Cl), or the benzo may have a benzo, pyrrolo, furyl or thienyl ring fused thereto, and the alkyl and alkoxy substituents may have from 1 to 5 (or 1 to 2) intervening oxygen, sulfur or nitrogen atoms. The phenyl ring of the styryl group may be further substituted with 1 to 4 substituents which are, independently, 1 to 18 carbon alkyl, aryl, heteroaryl, aryloxy or alkoxy, or halogen, and the alkyl and alkoxy substituents may have from 1 to 5 intervening oxygen, sulfur or nitrogen atoms.

The compounds of formula (A) may particularly be of formula (B) or formula (C) below:

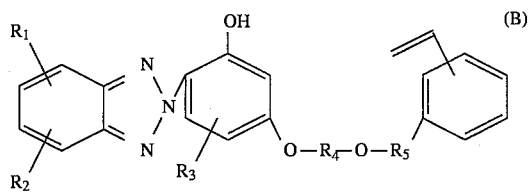

(B)

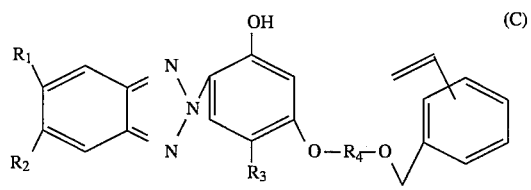

(C)

wherein:

$R_1$, $R_2$ and $R_3$ independently represent alkyl, alkoxy, aryl, heteroaryl, or aryloxy, any of the foregoing of which may be substituted or unsubstituted and the alkyl or alkoxy may contain from 1 to 5 intervening oxygen, sulfur or nitrogen atoms, or any of $R_1$, $R_2$ or $R_3$ is H or a halogen atom, or both $R_1$ and $R_2$ together form an aromatic or hetero aromatic ring which may be substituted or unsubstituted;

$R_4$ is a substituted or unsubstituted alkylene and has a total of 2 to 20 atoms including one to 6 intervening oxygen atoms. (preferably 2 or 4); and $R_5$ is a substituted or unsubstituted methylene.

More particularly, in any of the above formula (A), (B) or (C), $R_1$, $R_2$ and $R_3$ may be, independently, 1 to 18 (or 1 to 10, 1 to 6, or 1 to 2) carbon alkyl or alkoxy either of which may have 1–5 (or 1 or 2) intervening oxygen, sulfur or nitrogen atoms, or are aryl, heteroaryl, or aryloxy. $R_1$, $R_2$ and $R_3$ may also be, independently or any of the foregoing substituted with 1 to 17 (or 1 to 10, 1 to 6, or 1 or 2) carbon alkoxy, 1 to 17 (or 1 to 10, 1 to 6, or 1 or 2) carbon alkyl sulfide, 0 to 17 carbon amino (or 0 to 10, 0 to 6, or 0 to 2), or a halogen, or any of $R_1$, $R_2$ or $R_3$ may be H or a halogen (particularly chloro or fluoro) or both $R_1$ and $R_2$ together form a 5 to 18 carbon atom aryl or heteroaryl ring which may be unsubstituted or substituted with a 1 to 17 (or 1 to 10, 1 to 6, or 1 or 2) carbon atom alkyl or alkoxy, or a halogen.

$R_1$, $R_2$ and $R_3$ may also be, independently: a chloro; a fluoro; a hydroxy; a cyano; a nitro; an acylamino group (for example, an acetylamino group), carbamoyl, sulfonyl, sulfamoyl, sulfonamido, acyloxy (for example, an acetoxy group or a benzoyloxy group), or an oxycarbonyl group (for example, a methoxycarbonyl group, etc.), any of which may have 1 to 18 (or 1 to 10, 1 to 6, or 1 to 2) carbon atoms.

Also, $R_4$ and $R_5$ may independently particularly have a total of 2 to 20 (or 2 to 10, or 2 to 4) atoms and is an alkylene which may have 1–5 (or 1, 2 or 3) intervening oxygen, sulfur or nitrogen atoms, or any of the foregoing substituted with a 1 to 10 (or 1 to 6, or 1 or 2) carbon alkoxy, a 1 to 10 (or 1 to 6, or 1 or 2) carbon atom alkyl sulfide, 0 to 10 (or 0 to 6, or 0 to 2) carbon amino, or with halogen.

$R_5$ may particularly be a methylene or a methylene substituted with 1 to 6 (or 1, 2 or 3) carbon atom alkyl or alkoxy or a 0 to 6 (or 0, 1, 2, or 3) carbon atom amino, or halogen.

In the method of making a compound of formula (D), of the present invention, the benzo ring and hydroxy substituted phenyl ring may have among possible substituents, any of the substituents as described for the corresponding benzo and hydroxy substituted phenyl rings of formula (A), (B) or (C). Similarly, $L_1$ or $L_2$, when substituted, may have as substituents any of those described for $R_5$.

The method of making a compound of formula (D) may particularly be used for making a compound of formula (E) or (F) below:

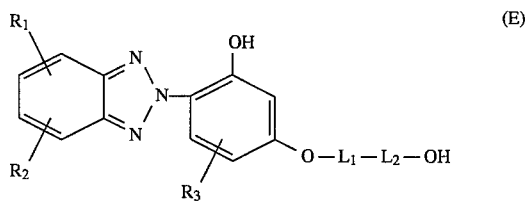

(E)

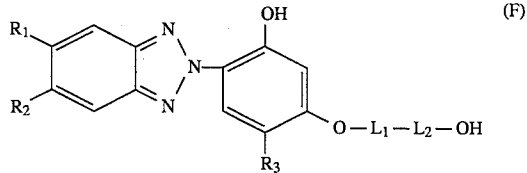

(F)

In formula (E) or (F), $R_1$, $R_2$, $R_3$ and $L_1$ and $L_2$ may be any of those groups already described above in connection with formula (A), (B), (C), or (D). Preferably, $L_1$ and $L_2$ are unsubstituted and $R_1$ and $R_2$ are, independently, hydrogen, methoxy, halogen (chloro or fluoro) in particular), and $R_3$ is H or 1–2 carbon alkyl (particularly ethyl) or chloro or fluoro.

Examples of any of the alkyl groups mentioned in relation to any of the formula herein, include a methyl group, an ethyl group, an n-propyl group, an isopropyl group, a butyl group, a tert-butyl group, an n-amyl group, an n-octyl group, a tert-octyl group, a methoxyethyl group, an ethoxyethyl group, a hydroxyethyl group, or a cyanoethyl group. Particular halogens where such are possible in any of the formula described herein, include fluorine, bromine and chlorine. Any aryl group includes, for example, a phenyl group, a tolyl group, a mesityl group, or the like. Examples of alkoxy are methoxy, an ethoxy, propoxy, butoxy group, ethoxyethoxy, or the like. Aryloxy includes, for example, a phenoxy group, or a 4-methylphenoxy group, or the like). An example of alkylthio is phenylthio. Examples of aminoalkyl include methylamino, ethylamino, and the like. An arylamino can include an anilino group.

As to the reaction for making compounds of formula (D) (which includes compounds of formula (E) or (F)), the reaction is preferably performed in the presence of a mono-, di-, tri- or tetra-alkyl ammonium or phosphonium compounds (preferably in the presence of a tetra-alkyl ammonium compound, that is a tetra-alkyl ammonium salt which is preferably tetramethyl ammonium chloride). Any of the foregoing alkyl groups of the alkyl ammonia compounds may independently particularly have from 1 to 8 (or 1 to 6, or 1 to 4) carbon atoms. The second phenolic OH group in the dihydroxy compounds corresponding to formula (D), (E) (that is formula (XII)) and (F), which undergoes selective monohydroxyethoxylation, could be substituted at any of these positions: 3', 4', 5', 4, 5, 6, or 7. Only the phenolic OH group at either 2' or 6' do not undergo hydroxyethoxylation due to a six-membered H-bonding with $N_1$ or $N_3$ atom in the benzotriazole ring. Because of the specifically desired UV absorbing characteristics, only the dihydroxy compounds corresponding to the compounds of formula (D), (E) or (F) having the second phenolic OH group at 4'-position in the phenyl ring, has been chosen as synthetic precursor in this invention.

Photographic elements of the present invention may contain UV absorbing polymers which have repeating units formed from the monomer of formula (A), anywhere within the element. Particularly, a photographic element according to the present invention will typically have at least one light sensitive silver halide emulsion layer and a non-light sensitive layer, with the ultraviolet absorbing polymer being located in the non-light sensitive layer. More preferably, a photographic element of the present invention will have the non-light sensitive layer containing the ultraviolet absorbing polymer located above all light sensitive layers. Any layer of the photographic element in which the UV absorbing polymers are located will normally be a gel layer, and the UV absorbing polymer may particularly be present therein in the form of a latex.

Photographic elements of the present invention may contain a UV absorbing polymer having only repeating units formed from the same formula selected from compounds within formula (A) (that is, the polymer is a homopolymer). Alternatively, the UV absorbing polymer may be a copolymer, containing repeating units formed from different monomers within formula (A) or containing, as well as repeating units formed from a monomer of formula (A), repeating units formed from other monomers not within formula (A). The copolymers may particularly include repeating units derived from acrylate, alkylacrylate, acrylamide, alykylacrylamide or vinyl aromatic monomers having a formula other than I. Particularly, a copolymer may contain units of the formula:

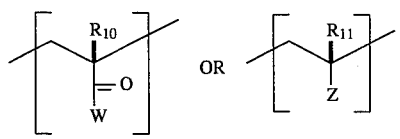

wherein: W is substituted or unsubstituted amino, substituted or unsubstituted alkoxy, substituted or unsubstituted phenoxy; Z is a substituted or unsubstituted phenyl; and $R_{10}$ and $R_{11}$ are H or a substituted or unsubstituted 1 to 6 carbon atom alkyl. Substituents in each case include halogen (for example, chloro, fluoro, bromo, iodo); or 1 to 12 (or 1 to 6, or 1 to 2) carbon alkoxy (for example, methoxy, ethoxy), alkyl (for example, methyl, trifluoromethyl), alkenyl, or thioalkyl (for example, methylthio or ethylthio); and 1 to 20 carbon atom aryl (for example, phenyl); heterocyclic structures (for example, thienyl, furyl, pyrrolyl), alkoxy and others known in the art.

Polymers containing repeating units formed from monomers of formula (A), can be provided in photographic elements in the form of a polymer latex. Polymer latexes may be prepared by emulsion polymerization which is well known in the art and is described in F. A. Bovey, Emulsion Polymerization, issued by Interscience Publishers Inc. New York, 1955. Examples of the chemical initiators which may be used include a thermally decomposable initiator, for example, a persulfate (such as ammonium persulfate, potassium persulfate, and the like), hydrogen peroxide, 4,4'-azobis(4-cyanovaleric acid), and redox initiators such as hydrogen peroxide-iron(II) salt, potassium persulfate-sodium hydrogensulfate, cerium salt-alcohol, etc. Emulsifiers which may be used in the emulsion polymerization include soap, a sulfonate(for example, sodium N-methyl-N-oleoyltaurate, etc.), a sulfate( for example, sodium dodecyl sulfate, etc.), a cationic compound(for example, hexadecyl trimethylammonium bromide, etc.), an amphoteric compound and a high molecular weight protective colloid(for example, polyvinyl alcohol, polyacrylic acid, gelatin, etc.). Specific examples and functions of the emulsifiers are described in Belgische Chemische Industrie, Vol. 28, pages 16–20(1963).

Emulsion polymerization of solid water-insoluble UV absorbing monomer is usually carried out in an aqueous system or a water/organic solvent system. Organic solvents which can be used are preferably those which have high water miscibility, are substantially inert to the monomers to be used, and do not interrupt usual reactions in free radical addition polymerization. Preferred examples include a lower alcohol having from 1 to 4 carbon atoms (for example, methanol, ethanol, isopropanol, etc.), a ketone (for example, acetone, etc.), a cyclic ether (for example, tetrahydrofuran, etc.), a nitrile (for example, acetonitrile,etc.), an amide (for example, N,N-dimethylforamide, etc.), a sulfoxide (for example, dimethylsulfoxide), and the like. This method is the most direct way of preparing a polymer latex as described in U.S. Pat. Nos. 4,464,462; 4,455,368 and European Patent publication 0 190 003 (1991).

Such polymer latexes can be loaded with other compounds such as high boiling point organic solvents or monomeric UV absorbing compounds. "Loading" a polymer latex is generally described in U.S. Pat. No. 4,199,363 for example. There are several methods of loading the high boiling point solvents into the polymer latex. First, an aqueous dispersion of a high boiling point solvent (or mixture of such solvents) is prepared by the conventional colloid mill process in the presence of gelatin. This dispersion is then blended with the polymer latex such that the weight ratio of high boiling, water immiscible organic solvent to polymer latex is between 0.1 to 5.0 (that is, 0.1/1 to 5.0/1 of solvent/polymer latex), and more preferably between 0.2 to 3.0 (that is, 0.2/1 to 3.0/1 of solvent/polymer latex).

In a second method of loading the polymer latex, the high boiling point solvent is loaded into the polymeric UV absorbing agent in the presence of low boiling organic solvents, such as methanol or acetone. The auxiliary solvent is then evaporated with a rotary evaporator. The same weight ratios of high boiling, water immiscible organic solvent can be used as in the above method.

Loading of a polymer latex is described, for example, in U.S. Pat. Nos. 4,203,716, 4,214,047, 4,247,627, 4,497,929 and 4,608,424.

Conventional UV absorbing agents can also be loaded into the UV absorbing polymer latexes of the photographic elements of the present invention to alter their photographic performance. Examples of such conventional UV absorbing agents which can be used include: 2-(2-hydroxy-5-methylphenyl)-2H-benzotriazole, 2-(2-hydroxy-3,5-di-tert-butylphenyl)-2H-benzotriazole, 2-(2-hydroxy-3-tert-butyl-5-methylphenyl)-2H-benzotriazole, 2-(2-hydroxy-3,5-di-tert-butylphenyl)-5-chloro-2H-benzotriazole, 2-(2-hydroxy-3,5-di-tert-amylphenyl)-2H-benzotriazole, 2-(2-hydroxy-3,5-di(1,1-dimethylbenzyl)-phenyl)-2H-benzotriazole, 2-(2-hydroxy-5-tert-octylphenyl)-2H-benzotriazole. Other types of UV absorbing agents such as p-hydroxybenzoates, phenylesters of benzoic acid, salicylanilides and oxanilides, diketones, benzylidene malonate, esters of α-cyano-cinnamic acid, and organic metal photostabilizers, and others, as described in J. F. Rabek, Photostabilization of Polymers, Principles and Applications, Elsevier Science Publishers LTD, England, page 202–278(1990).

The loaded or non-loaded polymer dispersion is incorporated into the photographic element (typically into a gelatin gel thereof) in an amount of between 0.2 g/m$^2$ to 10 g/m$^2$, and more preferably between 0.5 g/m$^2$ to 5.0 g/m$^2$. Furthermore, the weight ratio of high boiling, water immiscible organic solvent to polymer latex is preferably between 0.1 to 5.0 (that is, 0.1/1 to 5.0/1 of solvent/polymer latex), and more preferably between 0.2 to 3.0 (that is, 0.2/1 to 3.0/1 of solvent/polymer latex).

The polymer latex is provided in any one or more of the layers (for example, a hydrophilic colloid layer such as a gelatin layer) of a photographic light-sensitive material (for example, a silver halide photographic light-sensitive material), such as a surface protective layer, an intermediate layer or a silver halide emulsion layer, and the like. For example, in photographic paper the UV absorbing polymer latex may be positioned above and/or below the red sensitive layer (typically adjacent to it), the red sensitive layer typically being the uppermost light sensitive layer in color paper, or even completely or partially within the red sensitive layer. The latex is typically provided in a given layer of a photographic element by coating the hydrophilic colloid material (such as a gelatin emulsion) which contains the latex, onto a support or another previously coated layer forming part of the element.

The photographic elements made by the method of the present invention can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In a alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support which can be transparent or reflective (for example, a paper support). Photographic elements of the present invention may also usefully include a magnetic recording material as described in *Research Disclosure*, Item 34390, November 1992, or a transparent magnetic recording layer such as a layer containing magnetic particles on the underside of a transparent support as in U.S. Pat. Nos. 4,279,945 and 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, with the reverse order on a reflective support being typical.

The present invention also contemplates the use of photographic elements of the present invention in what are often referred to as single use cameras (or "film with lens" units). Such cameras may have glass or plastic lenses through which the photographic element is exposed.

In the following discussion of suitable materials for use in elements of this invention, reference will be made to Research Disclosure, December 1989, Item 308119, published by Kenneth Mason Publications, Ltd., Dudley Annex, 12a North Street, Emsworth, Hampshire P010 7DQ, ENGLAND, which will be identified hereafter by the term "Research Disclosure I." The Sections hereafter referred to are Sections of the Research Disclosure I.

The silver halide emulsions employed in the elements of this invention can be either negative-working, such as surface-sensitive emulsions or unfogged internal latent image forming emulsions, or direct positive emulsions of the unfogged, internal latent image forming type which are positive working when development is conducted with uniform light exposure or in the presence of a nucleating agent. Suitable emulsions and their preparation as well as methods of chemical and spectral sensitization are described in Sections I through IV. Color materials and development modifiers are described in Sections V and XXI. Vehicles which can be used in the elements of the present invention are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

With negative working silver halide a negative image can be formed. Optionally a positive (or reversal) image can be formed although a negative image is typically first formed.

The photographic elements of the present invention may also use colored couplers (e.g. to adjust levels of interlayer correction) and masking couplers such as those described in EP 213.490; Japanese Published Application 58-172,647; U.S. Pat. No. 2,983,608; German Application DE 2,706, 117C; U.K. Patent 1,530,272; Japanese Application A-113935; U.S. Pat. No. 4,070,191 and German Application DE 2,643,965. The masking couplers may be shifted or blocked.

The photographic elements may also contain materials that accelerate or otherwise modify the processing steps of bleaching or fixing to improve the quality of the image. Bleach accelerators described in EP 193,389; EP 301,477; U.S. Pat. Nos. 4,163,669; 4,865,956; and 4,923,784 are particularly useful. Also contemplated is the use of nucleating agents, development accelerators or their precursors (UK Patent 2,097,140; U.K. Patent 2,131,188); electron transfer agents (U.S. Pat. Nos. 4,859,578; 4,912,025); anti-fogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. Nos. 4,420,556; and 4,543, 323.) Also, the couplers may be blocked or coated in protected form as described, for example, in Japanese Application 61/258,249 or U.S. Pat. No. 5,019,492.

The photographic elements may further contain other image-modifying compounds such as "Developer Inhibitor-Releasing" compounds (DIR's). Useful additional DIR's for elements of the present invention, are known in the art and examples are described in U.S. Pat. Nos. 3,137,578; 3,148, 022; 3,148,062; 3,227,554; 3,384,657; 3,379,529; 3,615, 506; 3,617,291; 3,620,746; 3,701,783; 3,733,201; 4,049, 455; 4,095,984; 4,126,459; 4,149,886; 4,150,228; 4,211, 562; 4,248,962; 4,259,437; 4,362,878; 4,409,323; 4,477, 563; 4,782,012; 4,962,018; 4,500,634; 4,579,816; 4,607, 004; 4,618,571; 4,678,739; 4,746,600; 4,746,601; 4,791, 049; 4,857,447; 4,865,959; 4,880,342; 4,886,736; 4,937, 179; 4,946,767; 4,948,716; 4,952,485; 4,956,269; 4,959, 299; 4,966,835; 4,985,336 as well as in patent publications GB 1,560,240; GB 2,007,662; GB 2,032,914; GB 2,099, 167; DE 2,842,063, DE 2,937,127; DE 3,636,824; DE 3,644,416 as well as the following European Patent Publications: 272,573; 335,319; 336,411; 346,899; 362,870; 365, 252; 365,346; 373,382; 376,212; 377,463; 378,236; 384, 670; 396,486; 401,612; 401,613.

DIR compounds are also disclosed in "Developer-Inhibitor-Releasing (DIR) Couplers for Color Photography," C. R. Barr, J. R. Thirtle and P. W. Vittum in Photographic Science and Engineering, Vol. 13, p. 174 (1969), incorporated herein by reference.

It is also contemplated that the concepts of the present invention may be employed to obtain reflection color prints as described in Research Disclosure, November 1979, Item 18716, available from Kenneth Mason Publications, Ltd, Dudley Annex, 12a North Street, Emsworth, Hampshire P0101 7DQ, England, incorporated herein by reference. The emulsions and materials to form elements of the present invention, may be coated on pH adjusted support as described in U.S. Pat. No. 4,917,994; with epoxy solvents (EP 0 164 961); with additional stabilizers (as described, for example, in U.S. Pat. Nos. 4,346,165; 4,540,653 and 4,906, 559); with ballasted chelating agents such as those in U.S. Pat. No. 4,994,359 to reduce sensitivity to polyvalent cations such as calcium; and with stain reducing compounds such as described in U.S. Pat. Nos. 5,068,171 and 5,096,805. Other compounds useful in the elements of the invention are disclosed in Japanese Published Applications 83-09,959; 83-62,586; 90-072,629, 90-072,630; 90-072,632; 90-072, 633; 90-072,634; 90-077,822; 90-078,229; 90-078,230; 90-079,336; 90-079,338; 90-079,690; 90-079,691; 90-080, 487; 90-080,489; 90-080,490; 90-080,491; 90-080,492; 90-080,494; 90-085,928; 90-086,669; 90-086,670; 90-087, 361; 90-087,362; 90-087,363; 90-087,364; 90-088,096; 90-088,097; 90-093,662; 90-093,663; 90-093,664; 90-093, 665; 90-093,666; 90-093,668; 90-094,055; 90-094,056; 90-101,937; 90-103,409; 90-151,577.

The silver halide used in the photographic elements of the present invention may be silver iodobromide, silver bromide, silver chloride, silver chlorobromide, silver chloroiodobromide, and the like. The type of silver halide grains preferably include polymorphic, cubic, and octahedral. The grain size of the silver halide may have any distribution known to be useful in photographic compositions, and may be ether polydipersed or monodispersed. Particularly useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T=ECD/t^2$$

where

ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred to that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions tabular grains satisfying the stated thickness criteria above account for at least 70 percent of the total grain projected area. In the highest performance tabular grain emulsions tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire PO10 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The silver halide grains to be used in the invention may be prepared according to methods known in the art, such as those described in *Research Disclosure I* and James, *The Theory of the Photographic Process*. These include methods such as ammoniacal emulsion making, neutral or acid emulsion making, and others known in the art. These methods generally involve mixing a water soluble silver salt with a water soluble halide salt in the presence of a protective colloid, and controlling the temperature, pAg, pH values, etc., at suitable values during formation of the silver halide by precipitation.

The silver halide to be used in the invention may be advantageously subjected to chemical sensitization with noble metal (for example, gold) sensitizers, middle chalcogen (for example, sulfur) sensitizers, reduction sensitizers and others known in the art. Compounds and techniques useful for chemical sensitization of silver halide are known in the art and described in *Research Disclosure I* and the references cited therein.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in *Research Disclosure I*. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in *Research Disclosure I*. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 5 to 8, and temperatures of from 30° to 80° C., as illustrated in *Research Disclosure*, June 1975, item 13452 and U.S. Pat. No. 3,772,031.

The silver halide may be sensitized by sensitizing dyes by any method known in the art, such as described in *Research Disclosure I*. The dye may be added to an emulsion of the silver halide grains and a hydrophilic colloid at any time prior to (e.g., during or after chemical sensitization) or simultaneous with the coating of the emulsion on a photographic element. The dye/silver halide emulsion may be mixed with a dispersion of color image-forming coupler immediately before coating or in advance of coating (for example, 2 hours).

Photographic elements of the present invention are preferably imagewise exposed using any of the known techniques, including those described in *Research Disclosure I*, section XVIII. This typically involves exposure to light in the visible region of the spectrum, and typically such exposure is of a live image (versus a stored image such as a computer stored image) through a lens.

Photographic elements comprising the composition of the invention can be processed in any of a number of well-known photographic processes utilizing any of a number of well-known processing compositions, described, for example, in *Research Disclosure I*, or in James, *The Theory of the Photographic Process* 4th, 1977. In the case of processing a reversal color element, the element is first treated with a black and white developer followed by treatment with a color developer. Preferred color developing agents are p-phenylenediamines. Especially preferred are:

4-amino N,N-diethylaniline hydrochloride, 4-amino-3-methyl-N,N-diethylaniline hydrochloride, 4-amino-3-methyl-N-ethyl-N-(β-(methanesulfonamido) ethylaniline sesquisulfate hydrate, 4-amino-3-methyl-N-ethyl-N-(β-hydroxyethyl)aniline sulfate, 4-amino-3-β-(methanesulfonamido)ethyl-N,N-diethylaniline hydrochloride and 4-amino-N-ethyl-N-(2-methoxyethyl)-m-toluidine di-p-toluene sulfonic acid.

Development is followed by bleach-fixing, to remove silver or silver halide, washing and drying.

The present invention will be further described in the examples below.

The dihdroxy compounds corresponding to the compounds of formula (D), (E) and (F), can be prepared by the method corresponding to that for particular compounds (XVI) below. In particular, 2-(2',4'-dihydroxyphenyl)benzotriazoles (XII) were prepared by the procedures well documented in the art such as U.S. Pat. No. 3,072,585, European Patent Application 86300416, and U.S. Pat. No. 4,028,331. In Scheme 1 where $R_1$, $R_2$, and $R_3$ occupied the specifically designated positions, the product (XII) was renumbered as (XVI).

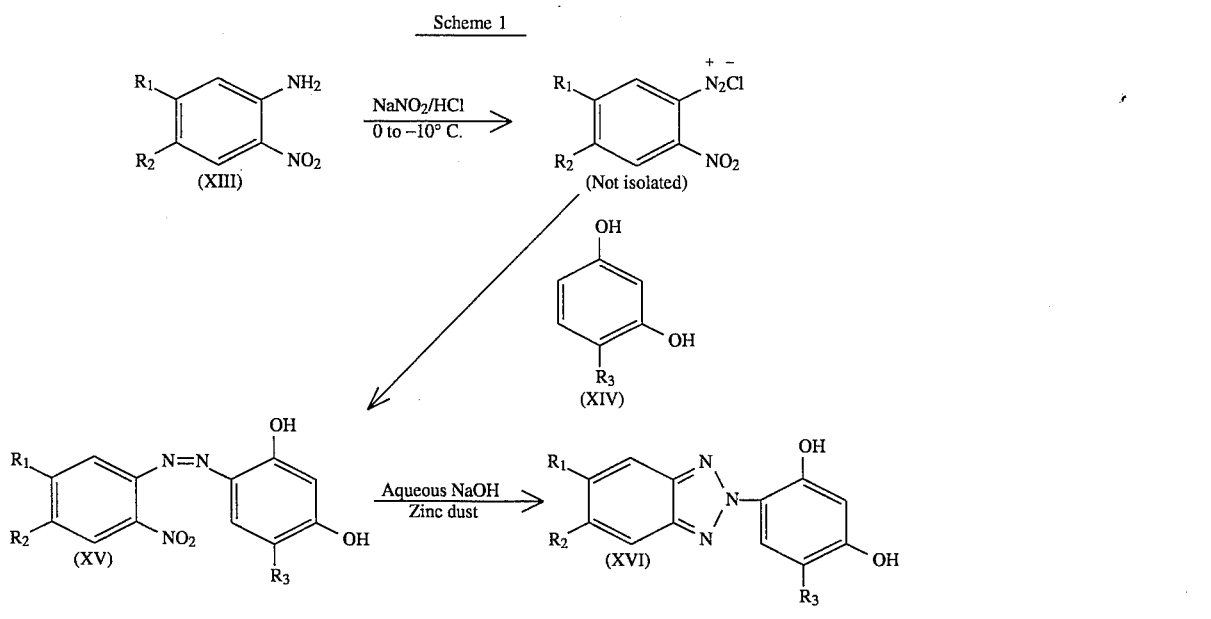

Scheme 1

Characteristics of particular azo dyes of formula (XV) prepared according to the foregoing method, are provided in Table 1 below. Throughout this application "$\lambda_{max}$" represents the wavelength of maximum absorption, "$\epsilon_{max}$" represents the extinction coefficient at $\lambda_{max}$, the "half bandwith" is the width of the absorption peak centered about $\lambda_{max}$ at the value of 50% of the maximum absorption, and "Comp. No." is the assigned compound number. Characteristics of the corresponding dihydroxy compounds of formula (XVI) are provided in Table 2 below.

TABLE 1

| Comp. No. | $R_1$ | $R_2$ | $R_3$ | % Yield | $\lambda_{max}$ (nm) (in MeOH) | $\epsilon_{max}$ (× 10⁴) | Half Bandwidth (nm) |
|---|---|---|---|---|---|---|---|
| XV-1 | H | H | H | 98 | 422 | 1.97 | 138 |
| XV-2 | H | Me | H | 99 | 416 | 1.89 | 145 |
| XV-3 | H | MeO | H | 87 | 408 | 1.95 | 136 |
| XV-4 | H | Cl | H | 99 | 436 | 1.74 | 141 |
| XV-5 | MeO | MeO | H | 93 | 454 | 2.00 | 197 |
| XV-6 | H | H | Et | 99 | 443 | 1.85 | 148 |
| XV-7 | H | H | Cl | 99 | — | — | — |

TABLE 2

| Comp. No. | $R_1$ | $R_2$ | $R_3$ | % Yield | $\lambda_{max}$ (nm) (in MeOH) | $\epsilon_{max}$ (× 10⁴) | Half Bandwidth (nm) |
|---|---|---|---|---|---|---|---|
| XVI-1 | H | H | H | 55–60 | 339 | 2.18 | 57 |
| XVI-2 | H | Me | H | 55–60 | 341 | 2.27 | 55 |
| XVI-3 | H | MeO | H | 40–50 | 346 | 2.46 | 53 |
| XVI-4 | H | Cl | H | 45–53 | 348 | 1.98 | 60 |
| XVI-5 | MeO | MeO | H | 35–45 | 346 | 2.94 | 52 |
| XVI-6 | H | H | Et | 46–55 | 348 | 2.12 | 59 |
| XVI-7 | H | H | Cl | 55–60 | 345 | 2.02 | 55 |

As already described above, in order to make new UV absorbing monomers (I) it was necessary to develop an economical, environmentally acceptable process for the preparation of 2-[2'-hydroxy, 4'-(2"-hydroxyethoxy)phenyl]-benzotriazoles (VII) by the selective hydroxyethoxylation of 2-(2',4'-dihydroxyphenyl)benzotriazoles (XVI). When $R_1$, $R_2$, and $R_3$ in (VII) occupy the specific positions in the respective rings, the structure (VII) was renumbered as (XVII).

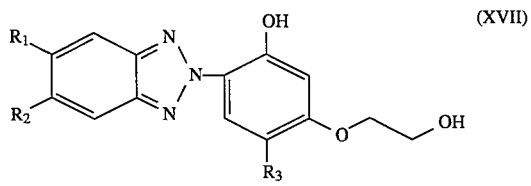

The process is carried out by reacting 2-(2',4'-dihydroxyphenyl)benzotriazoles (XVI), as outlined below (Scheme 2), with ethylene carbonate (VIII) in the presence of a catalyst, preferably a quaternary ammonium or phosphomium salt, at elevated temperatures. The product is subsequently isolated from the reaction mixture.

Scheme 2

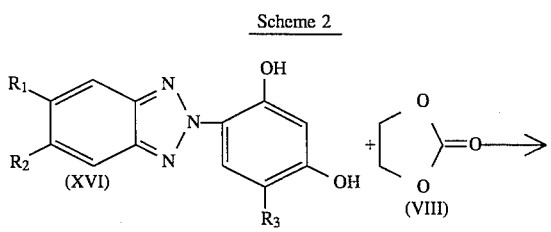

-continued
Scheme 2

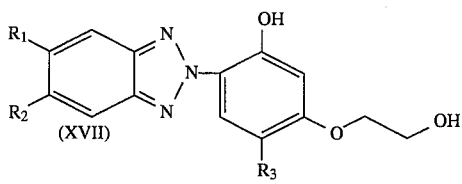

(XVII)

According to the process of the invention a number of 2-(2',4'-dihydroxyphenyl)benzotriazoles (XVI) may be employed as a reactant. $R_1$, $R_2$, and $R_3$ may have the same meaning as previously described.

The reaction of the benzotriazoles with ethylene carbonate can take place in the presence of solvents which are inert to the reactants, for examples in ethers such as diethyleneglycol dimethyl ether or anisole or in ketones such as 4-heptanone, but preferably is carried out solvent-free. Ethylene carbonate can be used in equal molar quantities (Scheme 2), in less than equal molar quantities or preferably in a slight excess. One generally uses from 0.95 to 1.5 moles of ethylene carbonate per mole of the benzotriazoles (XVI). Larger quantities are possible without additional advantages in using them.

Typical quaternary ammonium salts are practically all compounds of the type which are known from phase transfer reactions. Due to the overall suitability of the ammonium salts, the selection of a catalyst is governed primarily by its availability and price. Tetra alkyl ammonium or phosphomium salts are preferred. Economical tetramethyl ammonium chloride, for example, may also be used in this invention. Triethylamine, for example, may also be used, however, cleaner product is invariably obtained in better yield when tetramethylammonium chloride is used as a catalyst instead. The inefficiency of triethylamine may be attributed to high volatility causing its escape during heating.

The quantity of the catalyst is not particularly critical. Generally one can use from 0.1 to 0.001, more preferably from 0.02 to 0.05 moles of catalysts per mole of starting benzotriazoles (XVI). Larger quantities, for example 0.25 moles, are possible but are not required.

The reaction temperature is typically from 100° C. to 210° C., more preferably 120° C. to 200° C. For achieving a satisfactory reaction rate, temperatures above 140° C. are preferred. Possible side reactions are generally avoided below 180° C. Therefore, the optimum temperature range is regarded to be from 140° C. to about 175° C. Generally the reaction times range from 4 to about 16 hours.

Finishing the crude reaction mixture and isolating 2-[2'-hydroxy, 4'-(2"-hydroxyethoxy)phenyl]benzotriazoles (XVII; Table 3) can be accomplished in a conventional fashion, after the carbon dioxide evolution has terminated, by the addition of water or an organic solvent such as alcohols or acetone, and then by crystallizing the final product (XVII). When acetone is used as a solvent, the crude mixture could be poured in sufficient volume of brine solution for re precipitation and crystallization.

TABLE 3

| Comp. No. | $R_1$ | $R_2$ | $R_3$ | % Yield | $\lambda_{max}$ (nm) (in MeOH) | $\epsilon_{max}$ ($\times 10^4$) | Half Bandwidth (nm) |
|---|---|---|---|---|---|---|---|
| XVII-1 | H | H | H | 95 | 339 | 2.30 | 57 |
| XVII-2 | H | MeO | H | 90 | 346 | 2.60 | 52 |
| XVII-3 | H | Cl | H | 92 | 346 | 2.32 | 57 |
| XVII-4 | MeO | MeO | H | 88 | 346 | 3.19 | 51 |
| XVII-5 | H | H | Et | 97 | 347 | 2.16 | 58 |
| IVII-6 | H | H | Cl | 86 | 343 | 2.18 | 54 |

Generally, the finished materials (XVII) prepared according to said process precipitate out in sufficient purity, however an additional simple purification step may be added to the finishing process.

Good quality 2-[2'-hydroxy, 4'-(2"-hydroxyethoxy)phenyl]benzotriazoles are obtained when water is added to the reaction mixture upon completion. Then the pH is adjusted to about 10–12 using alkali such as sodium hydroxide and the reaction mixture is re-stirred for a short time (about 1 to 2 hours), preferably while heating to a temperatures from 90° C.–100° C. The reaction product is subsequently precipitated by acidifying the mixture to a pH of about 7 to 8, by adding mineral acids such as diluted hydrochloric acid or sulfuric acid. When using ammonium iodides as catalysts it may be advantageous to add a diluted sodium hydrogen sulfite solution after diluting the reaction with water.

Small scale samples of the crude product (XVII) could also be efficiently purified by silica gel flash column chromatography eluting with appropriate organic solvents or their mixture.

The following examples illustrate the various aspects of this invention but are not intended to limit its scope. The examples 1 through 5 are detailed process description of selective mono hydroxyethoxylation of 2-(2',4'-dihydroxyphenyl)benzotriazoles (XVI) to make compound (XVII).

EXAMPLE 1 (Compound No. XVII-1, Table 3).

A mixture of 45.4 g (0.2 mole) of 2-(2',4'-dihydroxyphenyl)benzotriazole, 19.8 g (0.225 mole) of ethylene carbonate and 0.55 g (0.005 mole) of tetramethylammonium chloride was heated under argon while stirring in an oil bath. The mixture changed to a brown melt as the temperature rose to 140° C. The argon gas flow was stopped at this point and the temperature was raised to 155° C. After the evolution of carbon dioxide stopped (7–8 hours), the reaction mixture was cooled to about 100° C. and then within 5 minutes 150 mL of water was added while stirring. The mixture was cooled to room temperature while stirring, at which point the semi-solid looking product crystallized. After suctioning off the solid, washing with water, and drying; 2-[2'-hydroxy, 4'-(2"-hydroxyethoxy)phenyl]benzotriazole was obtained having purity of 98% (HPLC). Yield: 51.5 g (95% of the theoretical).

It had important IR bands at 3448 (s, alcoholic OH), 2954, 1713, 1631, 1290, 1179, 1067 and 750 $cm^1$.

It had NMR peaks in ($CDCl_3$) at $\delta$ 11.40 (phenolic OH, s, 1H), 8.30 (d, 1H, arom.), 7.93 (broad singlet, 2H, arom), 7.42 (broad singlet, 2H, arom), 6.7 (s, 1H, arom.), 6.62 (d, 1H, arom.), 4.15 (broad singlet, 2H, Ar—O—$CH_2$), 4.0 (broad singlet, 2H, $CH_2OH$), 2.15 (broad split doublet, $CH_2$—OH, 1H, exchangeable with $D_2O$).

Calc. for $C_{14}H_{13}N_3O_3$: C, 61.99; H, 4.83; N, 15.49; M, 271.3 Found: C, 61.67; H, 4.83; N, 15.71; $M^+$, 271.

EXAMPLE 2 (Compound No. XVII-2, Table 3)

Following the procedure of Example 1, one obtained 54.2 g of 2-[2'-hydroxy, 4'-(2''-hydroxyethoxy)phenyl], 5-methoxybenzotriazole (90% of the theoretical amount) from 51.46 g (0.2 mole) of 5-methoxy-2-(2',4'-dihydroxyphenyl)benzotriazole, 19.8 g (0.225 mole) of ethylene carbonate and 0.55 g (0.005 mole) of tetramethylammonium chloride, after diluting with 150 mL of water.

It had important IR bands at 3378 (s, alcoholic OH), 3072, 2931, 1713, 1619, 1602, 1502, 1280, 1220, 1167, 1073 and 820 $cm^1$.

It had NMR peaks in ($CDCl_3$) at δ 11.70 (phenolic OH, s, 1H), 8.20 (d, 1H, arom.), 7.95 (d, 2H, arom), 7.10 (distorted doublet, 2H, arom), 6.7 (d, 1H, arom.), 6.60 (two doublets, 1H, arom.), 4.10 (t, 2H, Ar—O—$CH_2$), 4.0 (merged quartet, 2H, $CH_2OH$), 3.90(s, 3H, $OCH_3$), and 2.22 (broad singlet, 1H, $CH_2$—OH, exchangeable with $D_2O$).

Calc. for $C_{15}H_{15}N_3O_4$: C, 59.80; H, 5.02; N, 13.95; M, 301.3 Found: C, 59.11; H, 5.04; N, 13.84; $M^+$, 301.

EXAMPLE 3 (Compound No. XVII-3, Table 3)

Following the procedure of Example 1, one obtained 56.2 g of 2-[2'-hydroxy, 4'-(2''-hydroxyethoxy)phenyl], 5-chlorobenzotriazole (92% of the theoretical amount) from 52.34 g (0.2 mole) of 5-chloro-2-(2',4'-dihydroxyphenyl)benzotriazole, 19.8 g (0.225 mole) of ethylene carbonate and 0.55 g (0.005 mole) of tetramethylammonium chloride, after diluting with 150 mL of water.

It had important IR bands at 3519 (s, alcoholic OH), 3273, 3072, 2931, 2872, 1713, 1625, 1590, 1261, 1185, 1073, 1044, 826 and 797 $cm^1$.

It had NMR peaks in ($CDCl_3$) at δ 11.20 (phenolic OH, s, 1H), 8.22 (d, 1H, arom.), 7.9 (two doublets, 2H, arom), 7.48 (s, 1H, arom), 6.75 (d, 1H, arom.), 6.68 (two doublets, 1H, arom.), 4.15 (t, 2H, Ar—O—$CH_2$), 3.92(q, 2H, $CH_2OH$), and 2.73 (s, 1H, $CH_2$—OH, exchangeable with $D_2O$).

Calc. for $C_{14}H_{12}ClN_3O_3$: C, 55.00; H, 3.96; N, 13.74; Cl, 11.60, M, 305.7 Found: C, 55.93; H, 4.52; N, 13.36; Cl, 10.44, $M^+$, 305

EXAMPLE 4 (Compound No. 4, Table 3)

Following the procedure of Example 1, one obtained 58.3 g of 2-[2'-hydroxy, 4'-(2''-hydroxyethoxy)phenyl], 5,6-dimethoxybenzotriazole (88% of the theoretical amount) from 57.46 g (0.2 mole) of 5, 6-dimethoxy-2-(2',4'-dihydroxyphenyl)benzotriazole, 19.8 g (0.225 mole) of ethylene carbonate and 0.55 g (0.005 mole) of tetramethylammonium chloride, after diluting with 150 mL of water.

It had important IR bands at 3554 (s, alcoholic OH), 3507, 3436, 3083, 2942, 2830, 1713, 1625, 1595, 1513, 1280, 1367, 1284, 1214, 1166, 1070, and 1008 $cm^1$.

It had NMR peaks in ($CDCl_3$) at δ 11.35 (phenolic OH, s, 1H), 8.18 (d, 1H, arom.), 7.18 (s, 2H, arom), 6.65 (d, 1H, arom), 6.62 (two doublets, 1H, arom.), 4.15 (t, 2H, Ar—O—$CH_2$), 4.20 (m, merged with singlets of two $OCH_3$'s, 8H, one methylene+two methoxy groups), 2.1 (broad t, 1H, $CH_2$—OH, exchangeable with $D_2O$).

Calc. for $C_{16}H_{17}N_3O_5$: C, 58.00; H, 5.17; N, 12.68; M, 331.3 Found: C, 57.56; H, 5.21; N, 12.67; $M^+$, 331.

Now the intermediate compound (XVII) is appropriately functionalized for selective alkylation with vinyl benzyl chloride (XVIII) to give the inventive UV absorbing monomers (XIX) for polymerization and subsequent usage in silver halide photographic elements. In structure (XIX) $R_1$, $R_2$ and $R_3$ have the same meaning as already described in this invention.

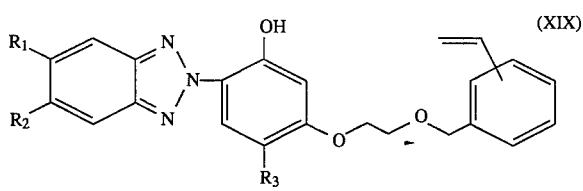

The commercially available vinyl benzyl chloride comes as a mixture of meta- and para- isomers, as a result, the inventive UV absorbing monomers (XIX) are obtained as same isomeric mixtures. We have found it advantageous to convert the intermediate (XVII) to alkali metal alkoxide (XVII') in situ before reacting with vinyl benzyl chloride (XVIII).

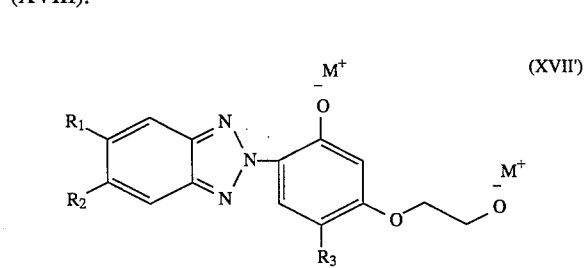

where $M^+$ is an alkali metal ion such as lithium, sodium, potassium, etc.

The bases such as sodium hydroxide, potassium hydroxide, cesium hydroxide, sodium t-butoxide, potassium t-butoxide, sodium hydride, or potassium hydride and suitable inert solvent such as dimethyl sulfoxide, sulfolane, dimethyl formamide, N,N-dimethyl acetamide, N-methyl pyrrolidinone, tetrahydrofuran, open chain mono or diethers, dioxane or any combination of these solvents may be advantageously used in alkylation of the intermediate (XVII) with vinyl benzyl chloride (XVIII). A suitable temperature may be chosen from a range of 25° C. to 100° C. which may depend on the solvent choice. Occasionally, dimethyl amino pyridine (DMAP) may be used as an effective catalyst in the alkylation step.

As in general it is well known that pKa of primary alkoxide ion is approximately twice as that of phenoxide ion (see "Advanced Organic Chemistry, Reactions, Mechanisms, and Structure", Third Edition, Jerry March, John Wiley & Sons, New York (1985), page 221, and reference numbers 40 & 47 cited thereon.), in structure (XVII') the nucleophilicity of the primary alkoxide ion will be several magnitudes higher than phenoxide ion toward vinyl benzyl chloride under SN2 type nucleophilic displacement reaction. [For a relationship between nucleophilic rates and pKa values; see, for example, Jokinen, Luukkonen, Ruostesuo, Virtanen, and Koskikallio, *Acta Chem. Scand.* 25, 3367 (1971); Bordwell and Hughes, *J. Org. Chem.*, 48, 2206 (1983)]. This property allows nearly exclusive alkylation of the primary alkoxide ion in structure (XVII') with vinyl benzyl chloride leading to desired UV absorbing monomers (XIX).

Specific representative examples of this alkylation leading to new UV absorbing monomers (XIX) are listed in Table 4. Nearly in each case after the alkylation the extinction coefficient increases approximately by 1000 compared to non-alkylated versions (see TABLE 3). The UV absorbing monomers with higher extinction coefficient, besides being effective UV absorbers at the desired wavelength, may be expected to offer some more cost advantage in the final photographic products.

TABLE 4

| Comp. No. | $R_1$ | $R_2$ | $R_3$ | % Yield | $\lambda_{max}$ (nm) (in MeOH) | $\epsilon_{max}$ ($\times 10^4$) | Half Band-width (nm) |
|---|---|---|---|---|---|---|---|
| XIX-1 | H | H | H | 98 | 338 | 2.40 | 57 |
| XIX-2 | H | MeO | H | 90 | 346 | 2.51 | 52 |
| XIX-3 | H | Cl | H | 92 | 346 | 2.45 | 58 |
| XIX-4 | MeO | MeO | H | 85 | 346 | 3.26 | 50 |
| XIX-5 | H | H | Et | 98 | 347 | 2.27 | 58 |
| XIX-6 | H | H | Cl | 89 | 343 | 2.37 | 55 |

Because the fused six-membered ring in the benzotriazole part of the structure (XIX) not being truly aromatic in character may behave like a cyclohexadiene system, any substituents containing an atom with a lone pair of electrons directly attached to the ring at 5 or 6 or at both positions such as alkoxy, aryloxy, or substituted or unsubstituted amino groups will make the system behave like fragile enol ether or enamine unit. The monomers (XIX) containing such substituents, therefore, may lose some intrinsic light stability. Although the intrinsic light stability may be recovered to some extent by converting the monomers into lower Tg (glass transition temperature) polymers. Although mono methoxy or dimethoxy substituents as in (XIX-2) and in (XIX-4), provide sharper batho cutting feature and higher extinction coefficient, this advantage may be reduced by their lower intrinsic light stability. The compounds (XIX-1), (XIX-3), (XIX-5), and (XIX-6) are the most useful compounds in the silver halide photographic elements.

The examples 6 through 10 are description of the detailed process for selective mono alkylation of (XVII) with vinyl benzyl chloride to make the UV absorbing monomers (XIX). Because the spectra of the inventive monomers will be compared with those of the mixture of the commonly used UV absorbers IIA and IIB in FIGS. 1 through 5, it is useful to list their absorption spectral characteristics here. All the spectra were measured in methanol.

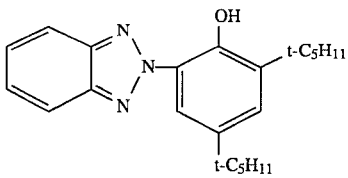

(IIA)

$\lambda_{max} = 341$ nm;
$\epsilon_{max} = 1.52 \times 10^4$ $\lambda_{max} = 302$ nm;
$\epsilon_{max} = 1.57 \times 10^4$

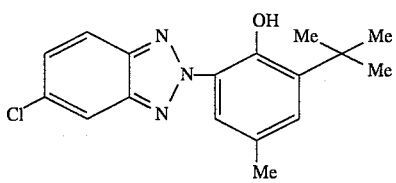

(IIB)

$\lambda_{max} = 348$ nm;
$\epsilon_{max} = 1.60 \times 10^4$ $\lambda_{max} = 309$ nm;
$\epsilon_{max} = 1.47 \times 10^4$ EXAMPLE 6 (Table 4, Compound No. XIX-1)

A mixture of 10.85 g (0.04 mole) of 2-[2',4'-(2"-hydroxyethoxy)phenyl]benzotriazole (Compound No. XVII-1 in Table 3), 0.15 g (0.0012 mole) of N,N-dimethylamino pyridine (as a catalyst), and 0.05 g of 2,6-di-t-butyl-4-methyl phenol (as a polymerization inhibitor) was taken in 500 mL of dry tetrahydrofuran and stirred magnetically under argon atmosphere. To this homogeneous reaction mixture, 9.1 g (0.081 mole) of potassium tert-butoxide was added all at once. This resulted to a deep yellow colored non-homogeneous reaction mixture. Then 7.0 g (0.046 mole, 6.6 mL) of vinyl benzyl chloride was added dropwise over 5 minutes. The deep yellow color of the reaction mixture changed to first light green then to pale yellow as the reaction progressed and as the temperature was raised from 25° C. to reflux. After 3 hours of reflux, it was cooled to room temperature. When the reaction mixture was acidified with 6 mL of glacial acetic acid, it became colorless. The solvent was removed on rotary evaporator. The residue was triturated with 50 mL of acetone and diluted with 800 mL of cold water. Insoluble product was filtered and air-dried. A 13.08 g yield (84% of the theoretical amount) was obtained. Its retention time in HPLC was 18.7 minute showing 100% purity by peak area percent. When this reaction was repeated in 150 mL of dry dimethyl sulfoxide (DMSO) at room temperature for 6 hours, 98% yield was obtained after pouring the reaction mixture in 1000 mL of cold water containing 6 mL of glacial acetic acid, filtering, washing with cold water and air-drying. Product was purified either by triturating in isopropanol or by flash column chromatography on silica gel by eluting with heptane/ethyl acetate (98/2) solvent mixture.

This monomer showed important IR (in KBr) bands at 3083, 2919, 2872, 1713, 1625, 1595, 1514, 1290, 1184, 1120, 1037 and 750 cm$^{-1}$. It had proton-nmr (in CDCl$_3$) peaks at $\delta$ 11.4 (s, 1H, phenolic OH), 8.24 (d, 1H, arom), 7.9 (two doublets, 2H, arom), 7.42 (m, 3H, arom), 7.35 (d, 2H, arom), 7.25 (s, 1H, arom), 6.73 (m, 2H, arom), 6.62 (m, 1H, vinylic), 5.78 (two doublets, 1H, vinylic proton), 5.25 (two doublets, 1H, vinylic proton), 4.68 (two singlets, 2H, benzylic $CH_2$, each peak representing meta- and para- isomer), 4.2 (t, 2H, CH2), and 3.84 (t, 2H, $CH_2$).

Calc. for $C_{23}H_{21}N_3O_3$: C, 71.30; H, 5.46; N, 10.85; M, 387.4 Found: C, 71.10; H, 4.92; N, 10.62; $M^+$, 387

The normalized absorbance spectra, in solution, of the monomer Compound No. XIX-1 and the mixture of commonly used UV absorbers IIA and IIB are compared in FIG. 1. A hypsochromic shift in the inventive compound XIX-1 will give a benefit of optical brightening effect and lower blue Dmin.

EXAMPLE 7 (TABLE 4, Compound No. XIX-2)

A mixture of 21.09 g (0.07 mole) of 2-[2',4'-( 2"-hydroxyethoxy)phenyl]-5-methoxybenzotriazole (Compound No. XVII-2 in Table 3), 0.15 g (0.0012 mole) of N,N-dimethylamino pyridine (as a catalyst), and 0.100 g of 2,6-di-t-butyl-4-methyl phenol (as a polymerization inhibitor) was taken in 500 mL of dry tetrahydrofuran and stirred magnetically under argon atmosphere. To this homogeneous reaction mixture, 15.94 g (0.142 mole) of potassium tert-butoxide was added all at once. This resulted to a deep yellow colored non-homogeneous reaction mixture. Then 12.36 g (0.081 mole, 11.5 mL) of vinyl benzyl chloride was added dropwise over 5 minutes. The deep yellow color of the reaction mixture changed to first light green then to pale yellow as the reaction progressed and as the temperature was raised from 25° C. to reflux. After 3 hours of reflux, it was cooled to room temperature. The solvent was removed on rotary evaporator. The residue was triturated with 100 mL of acetone and diluted with 1000 mL of cold water. Insoluble product was filtered and air-dried. A 26.86 g yield (92% of the theoretical amount) was obtained. Its TLC (Hexane/Ethyl Acetate; 7/3) showed Rf, 0.5. Its retention time in HPLC was 19 minute showing 100% purity by peak area percent. When this reaction was repeated in 150 mL of dry dimethyl sulfoxide (DMSO) at room temperature for 6 hours, 98% yield was obtained after pouring the reaction mixture in 1000 mL of cold water, neutralizing with glacial acetic acid for complete precipitation, filtering, washing with cold water and air-drying. Product was purified either by triturating in isopropanol or by flash column chromatography on silica gel by eluting with heptane/ethyl acetate (98/2) solvent mixture.

This monomer showed important IR (in KBr) bands at 3483, 3083, 3013, 2931, 2883, 2825, 1713, 1625, 1601, 1502, 1455, 1355, 1278, 1260, 1202, 1190, 1120, 1067, 1037, 896, 830, 803 and 726 $cm^{-1}$. It had proton-nmr (in $CDCl_3$) peaks at δ 11.4 (s, 1H, phenolic OH), 8.2 (d, 1H, arom), 7.72 (d, 1H, arom), 7.41 (d, 1H, arom), 7.4–7.21 (m, 3H, arom), 7.1 (d, 2H, arom), 6.8–6.6 (m, 3H, arom+1H vinylic), 5.78 (two doublets, 1H, vinylic proton), 5.22 (two doublets, 1H, vinylic proton), 4.62 (two singlets, 2H, benzylic $CH_2$, each peak representing meta- and para- isomer), 4.18 (t, 2H, CH2), 3.92 (s, 3H, $OCH_3$) and 3.83 (t, 2H, $CH_2$).

Calc. for $C_{24}H_{23}N_3O_4$: C, 69.05; H, 5.55; N, 10.07; M, 417.5 Found: C, 68.05; H, 5.45; N, 9.85; $M^+$, 417

Figure 2:
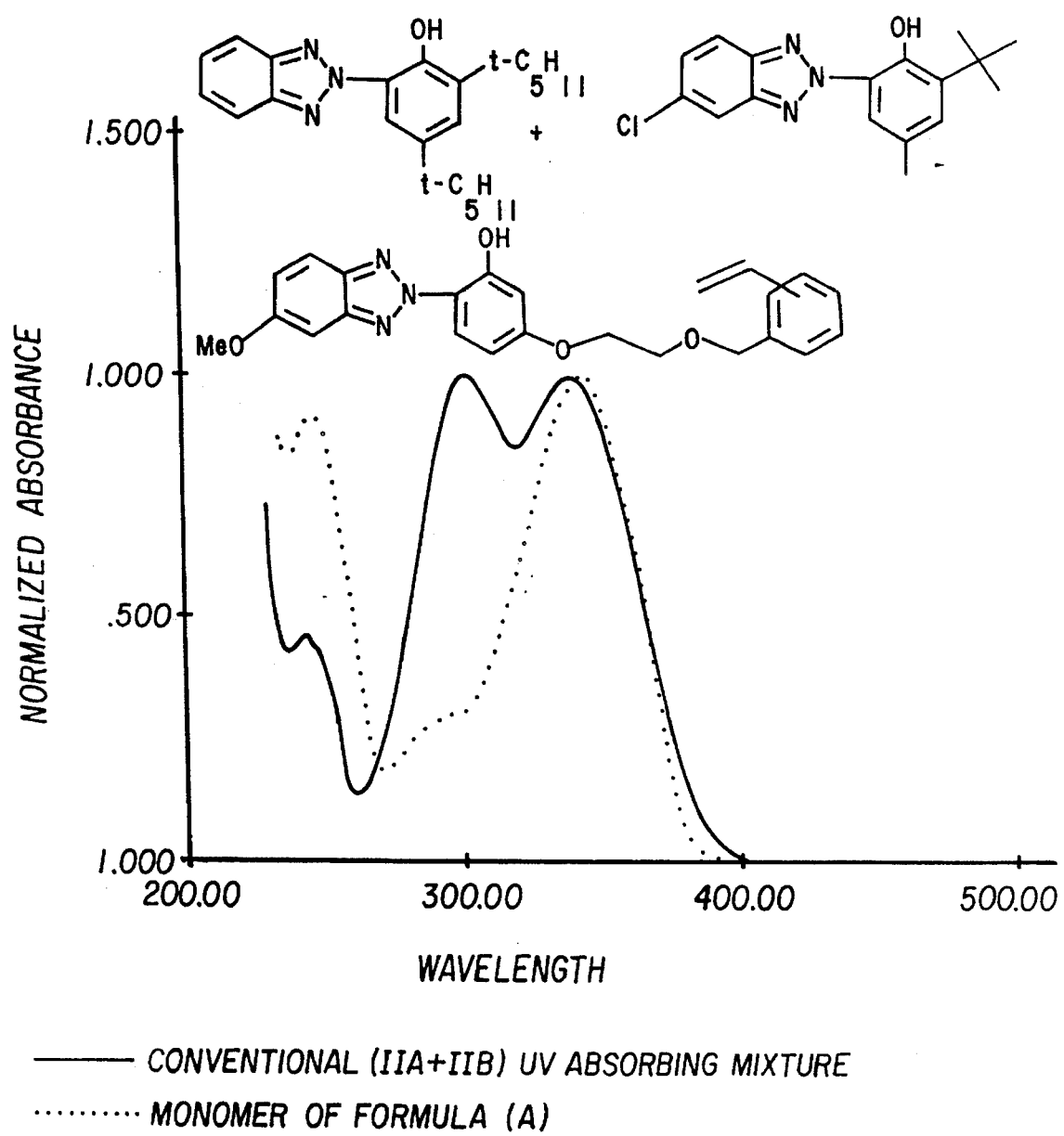
FIG. 2 shows the normalized absorbance spectra, in solution, of the monomer Compound No. XIX-2 of the present invention, described below, and a mixture of commonly used UV absorbers IIA and IIB.

The normalized absorbance spectra, in solution, of the monomer Compound No. XIX-2 and the mixture of commonly used UV absorbers IIA and IIB are compared in FIG. 2. A bathochromic shift in the inventive compound XIX-2 while maintaining overlap near 400 nm will give a benefit of nearly equal optical brightening effect and better protection for all image dyes, particularly for magenta image dye.

EXAMPLE 8 (TABLE 4, Compound No. XIX-3)

A mixture of 10.5 g (0.025 mole) of 2-[2',4'-( 2"-hydroxyethoxy)phenyl]-5-chlorobenzotriazole (Compound No. XVII-3 in Table 3), 0.15 g (0.0012 mole) of N,N-dimethylamino pyridine (as a catalyst), and 0.100 g of 2,6-di-t-butyl-4-methyl phenol (as a polymerization inhibitor) was taken in 500 mL of dry tetrahydrofuran and stirred magnetically under argon atmosphere. To this homogeneous reaction mixture, 5.7 g (0.051 mole) of pottasium tert-butoxide was added all at once. This resulted to a deep yellow colored non-homogeneous reaction mixture. Then 4.38 g (0.029 mole, 4.1 mL) of vinyl benzyl chloride was added dropwise over 5 minutes. The deep yellow color of the reaction mixture changed to first light green then to pale yellow as the reaction progressed and as the temperature was raised from 25° C. to reflux. After 3 hours of reflux, it was cooled to room temperature. It was neutralized with glacial acetic acid. The solvent was removed on rotary evaporator. The residue was triturated with 100 mL of acetone and diluted with 1000 mL of cold water. Insoluble product was filtered and air-dried. A 10.01 g yield (95% of the theoretical amount) was obtained. Its TLC (Hexane/Ethyl Acetate; 7/3) showed Rf, 0.65. Its retention time in HPLC was 20.1 minute showing 95.4% purity by peak area percent. Its melting point was 105°–107° C. When this reaction was repeated in 150 mL of dry dimethyl sulfoxide (DMSO) at room temperature for 6 hours, 97% yield was obtained after pouring the reaction mixture in 1000 mL of cold water, neutralizing with glacial acetic acid for complete precipitation, filtering, washing with cold water and air-drying. Product was purified either by triturating in isopropanol or by flash column chromatography on silica gel by eluting with heptane/ethyl acetate (98/2) solvent mixture.

This monomer showed important IR (in KBr) bands at 3448, 3083, 2870, 1713, 1625, 1601, 1590, 1555, 1510, 1296, 1175, 1120, 1055, 1035, 984, 803 and 714 $cm^{-1}$. It had proton-nmr (in $CDCl_3$) peaks at δ 11.2 (s, 1H, phenolic OH), 7.93 (d, 1H, arom), 7.85 (d, 1H, arom), 7.5–7.21 (m, 5H, arom), 6.8–6.6 (m, 3H, arom+ 1H vinylic), 5.78 (two doublets, 1H, vinylic proton), 5.28 (two doublets, 1H, vinylic proton), 4.64 (two singlets, 2H, benzylic $CH_2$, each peak representing meta- and para- isomer), 4.21 (t, 2H, CH2), and 3.84 (t, 2H, $CH_2$).

Calc. for $C_{23}H_{20}C_{11}N_3O_3$: C, 65.48; H, 4.78; N, 9.96; M, 421.9 Found: C, 64.51; H, 4.73; N, 9.90

Figure 3:
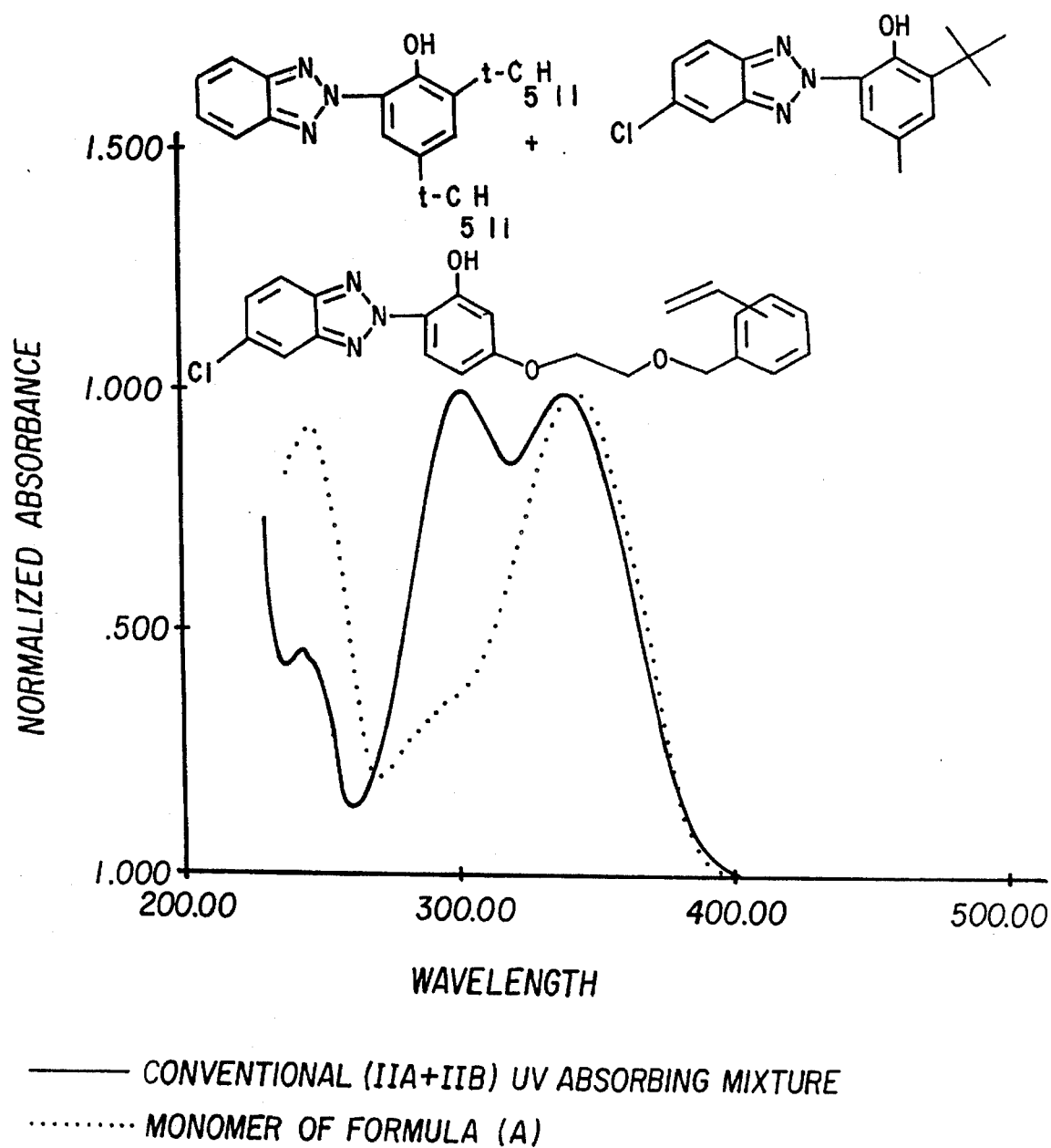
FIG. 3 shows the normalized absorbance spectra, in solution, of the monomer Compound No. XIX-3 of the present invention, described below, and a mixture of commonly used UV absorbers IIA and IIB.

The normalized absorbance spectra, in solution, of the monomer Compound No. XIX-3 and the mixture of commonly used UV absorbers IIA and IIB are compared in FIG. 3. A bathochromic shift in the inventive compound XIX-3 while maintaining overlap near 400 nm will give a benefit of nearly equal optical brightening effect and better protection for all image dyes, particularly for magenta image dye. Also inventive monomer XIX-3 offers an advantage of higher extinction coefficient.

EXAMPLE 9 (TABLE 4, Compound No. XIX-4)

A mixture of 9.94 g (0.03 mole) of 2-[2',4'-( 2"-hydroxyethoxy)phenyl]-5,6-dimethoxybenzotriazole (Compound No. XVII-4 in Table 3), 0.15 g (0.0012 mole) of N,N-dimethylamino pyridine (as a catalyst), and 0.100 g of 2,6-di-t-butyl-4-methyl phenol (as a polymerization inhibitor) was taken in 500 mL of dry tetrahydrofuran and stirred magnetically under argon atmosphere. To this homogeneous reaction mixture, 6.85 g (0.061 mole) of potassium tert-butoxide was added all at once. This resulted to a deep yellow colored non-homogeneous reaction mixture. Then 5.5 g (0.036 mole, 5.2 mL) of vinyl benzyl chloride was added dropwise over 5 minutes. The deep yellow color of the reaction mixture changed to first light green then to pale yellow as the reaction progressed and as the temperature was raised from 25° C. to reflux. After 1 hour of reflux, it was cooled to room temperature. It was neutralized with glacial acetic acid. The solvent was removed on rotary evaporator. The residue was triturated with 50 mL of acetone and diluted with 800 mL of cold water. Insoluble product was filtered and air-dried. A 12.79 g yield (95% of the theoretical amount) was obtained. Its TLC (Hexane/Ethyl Acetate; 7/3) showed Rf, 0.3. Its retention time in HPLC was 17.8 minute showing 100% purity by peak area percent. When this reaction was repeated in 100 mL of dry dimethyl sulfoxide (DMSO) at room temperature for 6 hours, 98% yield was obtained after pouring the reaction mixture in 1000 mL of cold water, neutralizing with glacial acetic acid for complete precipitation, filtering, washing with cold water and air-drying. Product was purified either by triturating in isopropanol or by flash column chromatography on silica gel by eluting with heptane/ethyl acetate (98/2) solvent mixture.

This monomer showed important IR (in KBr) bands at 3448, 3083, 2989, 2919, 2860, 2825, 1713, 1619, 1602, 1566, 1502, 1267, 1208, 1108, 902 and 820 cm$^{-1}$. It had proton-nmr (in CDCl$_3$) peaks at δ 11.3 (s, 1H, phenolic OH), 8.15 (d, 1H, arom), 7.42–7.20 (m, 4H, arom), 7.1 (s, 2H, arom), 6.78–6.58 (m, 3H, arom+ 1H vinylic), 5.75 (two doublets, 1H, vinylic proton), 5.25 (two doublets, 1H, vinylic proton), 4.63 (two singlets, 2H, benzylic CH$_2$, each peak representing meta- and para- isomer), 4.20 (t, 2H, CH2), 4.0 (s, 6H, 2×OCH$_3$) and 3.85 (t, 2H, CH$_2$).

Calc. for $C_{25}H_{25}N_3O_5$: C, 67.10; H, 5.63; N, 9.39; M, 447.5 Found: C, 66.32; H, 5.45; N, 9.27; M$^+$, 447

Figure 4:
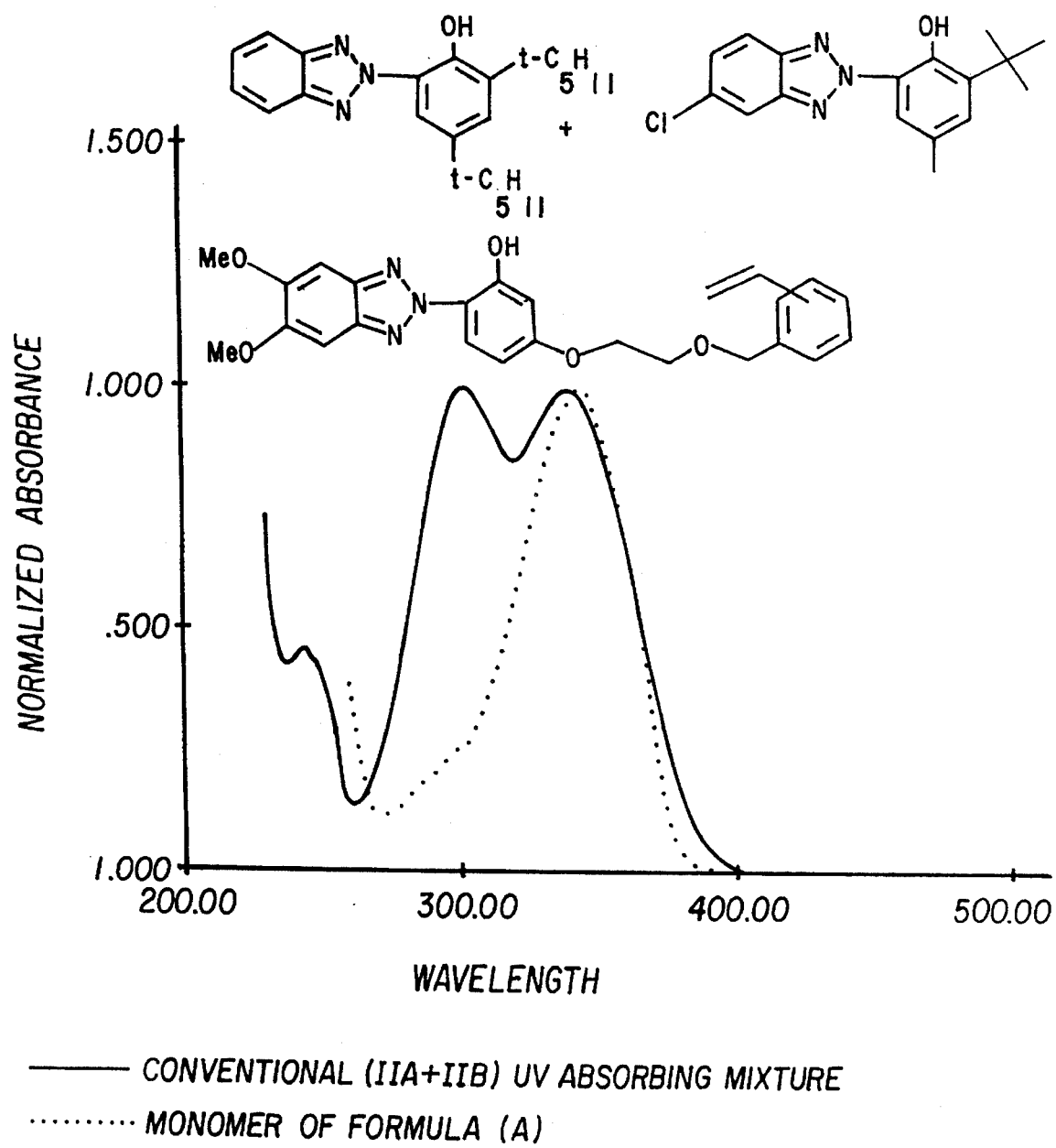
FIG. 4 shows the normalized absorbance spectra, in solution, of the monomer Compound No. XIX-4 of the present invention, described below, and a mixture of commonly used UV absorbers IIA and IIB.

The normalized absorbance spectra, in solution, of the monomer Compound No. XIX-4 and the mixture of commonly used UV absorbers IIA and IIB are compared in FIG. 4. A bathochromic shift in the inventive compound XIX-4 while maintaining overlap near 400 nm will give a benefit of nearly equal optical brightening effect and better protection for all image dyes, particularly for magenta image dye. Also inventive monomer XIX-4 offers an advantage of higher extinction coefficient.

EXAMPLE 10 (TABLE 4, Compound No. XIX-5)

A mixture of 17.96 g (0.06 mole) of 2-[2',4'-(2"-hydroxyethoxy), 5'-ethyl phenyl]benzotriazole (Compound No. XVII-5 in Table 3), 0.15 g (0.0012 mole) of N,N-dimethylamino pyridine (as a catalyst), and 0.100 g of 2,6-di-t-butyl-4-methyl phenol (as a polymerization inhibitor) was taken in 500 mL of dry tetrahydrofuran and stirred magnetically under argon atmosphere. To this homogeneous reaction mixture, 13.8 g (0.123 mole of potassium tert-butoxide) was added all at once. This resulted to a deep yellow colored non-homogeneous reaction mixture. Then 10.8 g (0.071 mole, 10 mL) of vinyl benzyl chloride was added dropwise over 5 minutes. The deep yellow color of the reaction mixture changed to first light green then to pale yellow as the reaction progressed and as the temperature was raised from 25° C. to reflux. After 2 hour of reflux, it was cooled to room temperature. It was neutralized with glacial acetic acid. The solvent was removed on rotary evaporator. The residue was triturated with 50 mL of acetone and diluted with 1000 mL of cold water. Insoluble product was filtered and air-dried. A 22.2 g yield (89% of the theoretical amount) was obtained. Its TLC (Hexane/Ethyl Acetate; 7/3) showed Rf, 0.5. Its retention time in HPLC was 20.8 minute showing 100% purity by peak area percent. When this reaction was repeated in 100 mL of dry dimethyl sulfoxide (DMSO) at room temperature for 6 hours, 98% yield was obtained after pouring the reaction mixture in 1000 mL of cold water, neutralizing with glacial acetic acid for complete precipitation, filtering, washing with cold water and air-drying. Product was purified either by triturating in isopropanol or by flash column chromatography on silica gel by eluting with heptane/ethyl acetate (95/5) solvent mixture.

This monomer showed important IR (in KBr) bands at 3048, 2954, 2919, 2872, 1713, 1631, 1602, 1496, 1440, 1280, 1250, 1190, 1125, 1067, 902, 830 and 744 cm$^{-1}$. It had proton-nmr (in CDCl$_3$) peaks at δ 11.3 (s, 1H, phenolic OH), 8.15 (d, 1H, arom), 7.90 (two doublets, 2H, arom.), 7.57–7.20 (m, 6H, arom.), 6.7 (two doublets, 1H, vinylic), 6.65 (s, 1H, arom.), 5.78 (two doublets, 1H, vinylic proton), 5.25 (two doublets, 1H, vinylic proton), 4.62 (two singlets, 2H, benzylic CH$_2$, each peak representing meta- and para-isomer), 4.22 (t, 2H, CH2), 3.9 (t, 2H, CH2), 2.7 (q, 2H, CH$_2$–CH$_3$), and 1.28 (t, 3H, CH$_2$–CH$_3$).

Calc. for $C_{25}H_{25}N_3O_3$: C, 72.27; H, 6.06; N, 10.11; M, 415.5 Found: C,71.85; H, 5.89; N, 10.19

Figure 5:
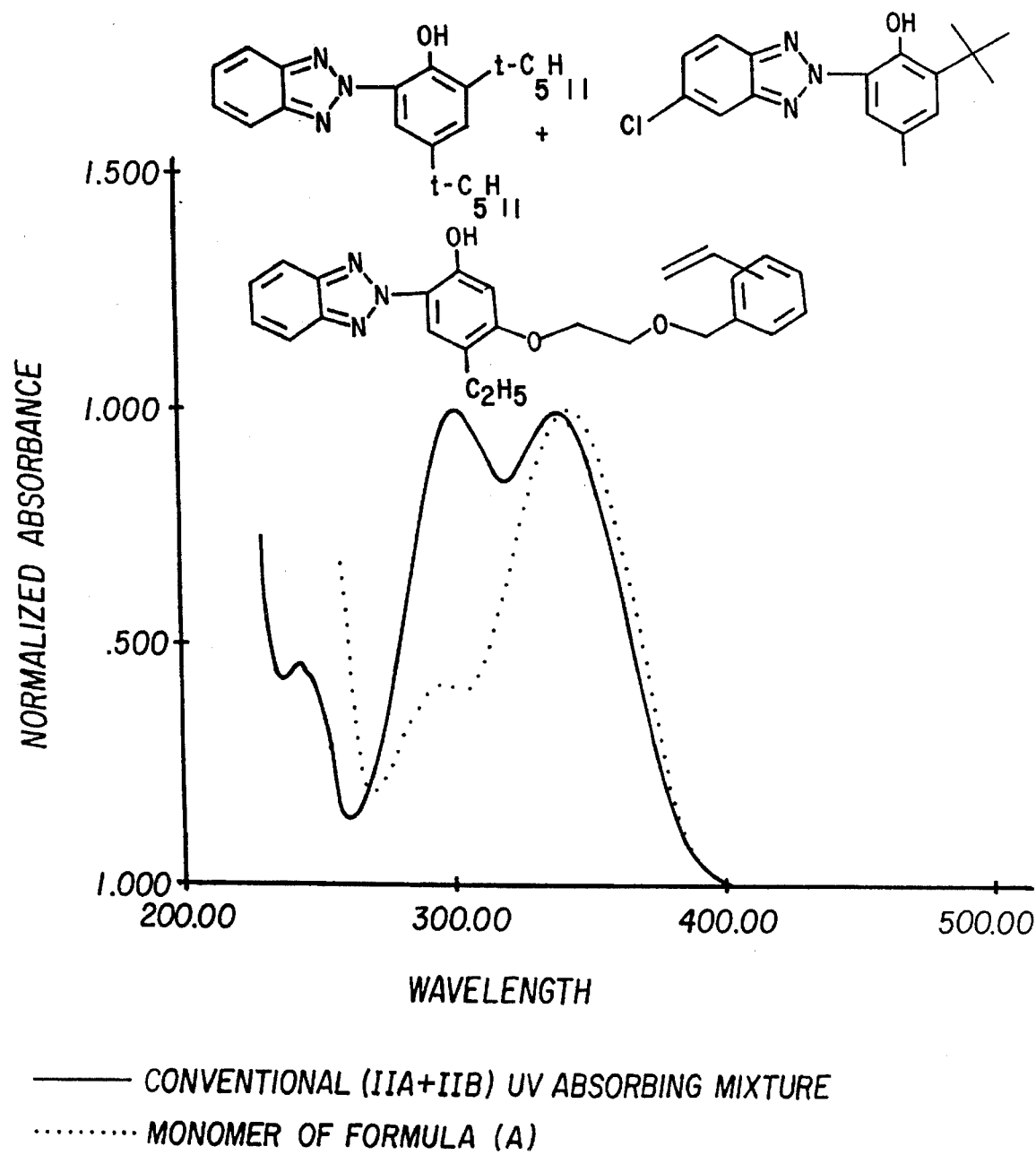
FIG. 5 shows the normalized absorbance spectra, in solution, of the monomer Compound No. XIX-5 of the present invention, described below, and a mixture of commonly used UV absorbers IIA and IIB.

The normalized absorbance spectra, in solution, of the monomer Compound No. XIX-5 and the mixture of commonly used UV absorbers IIA and IIB are compared in FIG. 5. A bathochromic shift in the inventive compound XIX-5 while maintaining overlap near 400 nm will give a benefit of nearly equal optical brightening effect and better protection for all image dyes, particularly for magenta image dye. Also inventive monomer XIX-4 offers an advantage of higher extinction coefficient.

The normalized absorbance spectra, in solution, of the monomer Compound No. XIX-1 and the mixture of commonly used UV absorbers IIA and IIB are compared in FIG. 1. A hypsochromic shift in the inventive compound XIX-1 will give a benefit of optical brightening effect and lower blue Dmin.

The normalized absorbance spectra, in solution, of the monomer Compound No. XIX-2 and the mixture of commonly used UV absorbers IIA and IIB are compared in FIG. 2. A bathochromic shift in the inventive compound XIX-2 while maintaining overlap near 400 nm will give a benefit of nearly equal optical brightening effect and better protection for all image dyes, particularly for magenta image dye.

The normalized absorbance spectra, in solution, of the monomer Compound No. XIX-3 and the mixture of commonly used UV absorbers IIA and IIB are compared in FIG. 3. A bathochromic shift in the inventive compound XIX-3 while maintaining overlap near 400 nm will give a benefit of nearly equal optical brightening effect and better protection for all image dyes, particularly for magenta image dye. Also inventive monomer XIX-3 offers an advantage of higher extinction coefficient.

The normalized absorbance spectra, in solution, of the monomer Compound No. XIX-4 and the mixture of commonly used UV absorbers IIA and IIB are compared in FIG. 4. A bathochromic shift in the inventive compound XIX-4 while maintaining overlap near 400 nm will give a benefit of nearly equal optical brightening effect and better protection for all image dyes, particularly for magenta image dye. Also inventive monomer XIX-4 offers an advantage of higher extinction coefficient.

The normalized absorbance spectra, in solution, of the monomer Compound No. XIX-5 and an mixture of commonly used UV absorbers IIA and IIB are compared in FIG. 5. A bathochromic shift in the inventive compound XIX-5 while maintaining overlap near 400 nm will give a benefit of nearly equal optical brightening effect and better protection for all image dyes, particularly for magenta image dye. Also inventive monomer XIX-4 offers an advantage of higher extinction coefficient.

The preceding examples are set forth to illustrate specific embodiments of this invention and are not intended to limit the scope of the compositions or materials of the invention. It will be understood that variations and modifications can be effected within the spirit and scope of the invention.

I claim:

1. A photographic element comprising an ultraviolet absorbing polymer having repeating units formed from the monomer of formula (A):

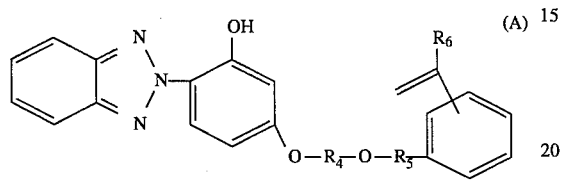

wherein: $R_4$ and $R_5$ are, independently, a substituted or unsubstituted alkylene with or without intervening oxygen, sulfur or nitrogen atoms, wherein the substituents are selected from a 1 to 10 carbon alkoxy, a 1 to 10 carbon atom alkyl sulfide, 0 to 10 carbon amino, and halogen; $R_6$ is H or an unsubstituted methyl or methyl substituted With a halogen; and the benzo ring, the hydroxy substituted phenyl ring, and the phenyl ring of the styryl group may be further substituted with 1 to 4 substituents or unsubstituted provided none of the further substituents have unsaturated carbon-carbon bonds, and wherein the subsituents are selected from 1 to 18 carbon alkyl, aryl, heteroaryl, aryloxy or alkoxy, or halogen, and the alkyl and alkoxy substituents may have from 1 to 5 intervening oxygen, sulfur or nitrogen atoms, or the benzo ring may have a benzo, pyrrolo, furyl, or thienyl ring fused thereto.

2. A photographic element according to claim 1 additionally comprising at least one gel layer, the ultraviolet absorbing polymer being incorporated into the gel layer in the form of a latex.

3. A photographic element according to claim 1 wherein the ultraviolet absorbing polymer is a copolymer.

4. A photographic element according to claim 1 wherein the ratio of monomeric units from formula (I) to other monomeric units is between 10:1 to 1:10.

5. A photographic element according to claim 1, the element additionally comprising at least one light sensitive silver halide emulsion layer and a non-light sensitive layer, wherein the ultraviolet absorbing polymer is located in the non-light sensitive layer.

6. A photographic element comprising a light-sensitive silver halide emulsion layer and an ultraviolet absorbing polymer present in the light-sensitive layer or another layer of the element, the ultraviolet absorbing polymer having repeating units formed from the monomer of formula (B):

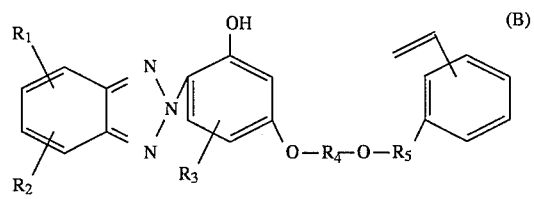

wherein:

$R_1$, $R_2$ and $R_3$ independently represent alkyl, alkoxy, aryl, heteroaryl, or aryloxy, any of the foregoing of which may be substituted or unsubstituted and the alkyl or alkoxy may contain from 1 to 5 intervening oxygen, sulfur or nitrogen atoms, wherein the substituents are selected from 1 to 17 carbon alkoxy, 1 to 17 carbon alkyl sulfide, 0 to 17 carbon amino, or a halogen; or any of $R_1$, $R_2$ or $R_3$ is H or a halogen atom, or both $R_1$ and $R_2$ together form an aromatic or hetero aromatic ring which may be unsubstituted or substituted with with a 1 to 17 carbon atom alkyl or alkoxy, or a halogen;

$R_4$ is a substituted or unsubstituted alkylene and has a total of 2 to 20 atoms, wherein the substituents are selected from a 1 to 10 carbon alkoxy, a 1 to 10 carbon atom alkyl sulfide, 0 to 10 carbon amino, and halogen; and $R_5$ is a substituted or unsubstituted methylene, wherein the substituents are selected from a 1 to 10 carbon alkoxy, a 1 to 10 carbon atom alkyl sulfide, 0 to 10 carbon amino, and halogen.

7. A photographic element according to claim 6 wherein each of $R_1$, $R_2$ and $R_3$, is alkyl, alkoxy, H or halogen.

8. A photographic element according to claim 6 wherein $R_1$, $R_2$ and $R_3$ are, independently, 1 to 20 carbon atom alkyl or alkoxy, either of which may be substituted or unsubstituted, or H or halogen.

9. A photographic element according to claim 6, the element additionally comprising at least one light sensitive silver halide emulsion layer and a non-light sensitive layer, wherein the ultraviolet absorbing polymer is located in the non-light sensitive layer.

10. A photographic element according to claim 6 wherein the non-light sensitive layer containing the ultraviolet absorbing polymer is located above all light sensitive layers.

11. A photographic element according to claim 6 wherein the monomer of formula (B) has the following formula:

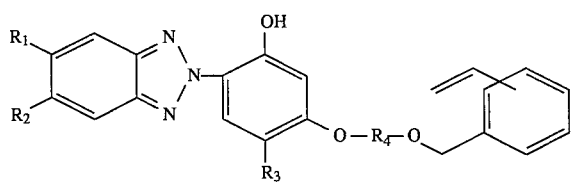

12. A photographic element according to claim 6 wherein $R_1$, $R_2$ and $R_3$ are, independently, 1 to 6 carbon atom alkyl or alkoxy, either of which may be substituted or unsubstituted, or H or halogen.

\* \* \* \* \*